US011596509B2

(12) United States Patent
Nguyen

(10) Patent No.: US 11,596,509 B2
(45) Date of Patent: Mar. 7, 2023

(54) INLINE AVIAN SPRAY APPLICATOR WITH RAPIDLY-ACTUATING AUTOMATIC SPRAY NOZZLES

(71) Applicant: BOEHRINGER INGELHEIM ANIMAL HEALTH USA INC., Duluth, GA (US)

(72) Inventor: Chien Dinh Nguyen, Braselton, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 691 days.

(21) Appl. No.: 15/160,614

(22) Filed: May 20, 2016

(65) Prior Publication Data

US 2016/0338815 A1 Nov. 24, 2016

Related U.S. Application Data

(60) Provisional application No. 62/163,999, filed on May 20, 2015.

(51) Int. Cl.

| | |
|---|---|
| *A61D 1/02* | (2006.01) |
| *A61D 7/00* | (2006.01) |
| *A01K 45/00* | (2006.01) |
| *A23L 33/135* | (2016.01) |
| *A01K 39/00* | (2006.01) |
| *A61M 11/02* | (2006.01) |

(52) U.S. Cl.

CPC .............. *A61D 1/025* (2013.01); *A01K 39/00* (2013.01); *A01K 45/00* (2013.01); *A01K 45/002* (2013.01); *A23L 33/135* (2016.08); *A61D 7/00* (2013.01); *A61M 11/02* (2013.01); *A61M 2205/18* (2013.01); *A61M 2205/50* (2013.01); *A61M 2205/505* (2013.01); *A61M 2205/587* (2013.01)

(58) Field of Classification Search

CPC ................................ A61D 7/00; A61D 1/025

See application file for complete search history.

(56) References Cited

U.S. PATENT DOCUMENTS

| | | | | |
|---|---|---|---|---|
| 4,449,968 | A * | 5/1984 | Peterson | A61D 1/025 604/24 |
| 6,910,446 | B2 | 6/2005 | Johnston Jr. | |
| 8,794,185 | B2 | 8/2014 | Lee | |
| 2002/0104485 | A1 | 8/2002 | Lewis et al. | |
| 2002/0133886 | A1 * | 9/2002 | Severns | B01J 20/28033 8/142 |
| 2008/0195064 | A1 | 8/2008 | Correa et al. | |
| 2014/0288492 | A1 | 9/2014 | Kumar | |

FOREIGN PATENT DOCUMENTS

| | | |
|---|---|---|
| CN | 202 136 444 | 2/2012 |
| CN | 104 523 350 | 4/2015 |

OTHER PUBLICATIONS

Spraying System Co: "Autojet Model 1550+ Modular Spray System Automatic Spray Control Made Simple", Bulletin N°. 6260, Jan. 1, 2013 (Jan. 1, 2013 ), XP055301376, Wheaton, IL 60187-7901 USA Retrieved from the Internet: www.spray.com/literature_pdfs/B626D_AutoJet_1550-plus_Modular_Spray_System.pdf.

* cited by examiner

*Primary Examiner* — Jessica B Wong

(74) *Attorney, Agent, or Firm* — Jamie L. Graham

(57) ABSTRACT

The invention relates to spray applicator devices and methods of use for vaccinating, or administering probiotics to, avian animals.

16 Claims, 13 Drawing Sheets

INLINE AVIAN SPRAY APPLICATOR WITH RAPIDLY-ACTUATING AUTOMATIC SPRAY NOZZLES

CROSS-REFERENCE TO OTHER APPLICATIONS

This application claims priority to US provisional patent application serial No. U.S. Ser. No. 62/163,999, filed on 20 May 2015, and herein incorporated by reference in its entirety.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention and does not reflect any view of the validity, patentability and/or enforceability of such cited patent documents.

FIELD OF THE INVENTION

The invention relates to inline spray applicator devices and methods of use for vaccinating and/or administering probiotics to avian animals.

BACKGROUND OF THE INVENTION

Inline spray applicators allow for rapid vaccination of young avian animal, for example, one day old chicks. Existing systems use flat nozzle technology to apply, in a non-stop process, a homogeneous spray pattern with constant droplet size and crate coverage. Known spray applicators for include, for example, Peterson et al., US patent publication number 4316464; Lee, Eng-Hong, Canadian patent publication number CA2416726; Lee, Eng-Hong, PCT patent publication number WO 2005/099617; Joseph H., Johnson, US patent publication number U.S. Pat. No. 6,910,446; Lewis et al., US patent publication number US 2002/0104485; and Sliter et al., US patent publication number 5404922.

However, since the speed of conveyors varies across poultry housing facilities, it would be desirable to regulate the amount of vaccine delivered over time, to improve vaccination efficacy and to reduce vaccine waste. Changing pressure would be one way to accomplish this regulation. However, increasing or decreasing pressure to a spray nozzle has the unwanted effect of changing the droplet size away from the desirable range of about 150 μM to about 250 μM.

Another possibility would be to use actuatable spray nozzles, which have the ability to rapidly cycle between on and off states. However, until the instant disclosure, it was not known whether vaccine and/or probiotics could be effectively delivered—without significantly altering droplet size—using actuatable spray nozzles. Applicants thus sought out to test whether such device could be developed.

SUMMARY OF THE INVENTION

The instant invention is based upon the successful blending of technologies from two different fields of endeavor: industrial spray coating and vaccination. The instant disclosure provides an improved apparatus for the spray vaccination of, and/or administration of probiotics to, avian animals, including day old chicks.

In an embodiment, the apparatus comprises an inline spray applicator system, comprising a modular spray system, comprising one or more rapidly actuating automatic spray nozzles. As used herein, the term "automatic spray nozzle" refers to a "nozzle assembly," which is a mechanical combination of a fixed, non-automatic nozzle "tip," and an electric, pneumatic or hydraulic actuating means. The nozzle tip is operably connected to, mounted on, or otherwise a component of, the actuating means. The nozzle tip may be sealably connected to the actuating portion of the automatic spray nozzle via a high pressure tip retainer, a tip gasket, a screen strainer, another gasket and a high pressure female body (i.e. the components used to affix UniJet® spray nozzles to their corresponding actuators). The actuating means functions by reversibly permitting or blocking fluid flow to the nozzle tip. It is thus the actuating means that makes an otherwise non-automatic, fixed nozzle tip an "automatic nozzle." The skilled person understands that multiple routine combinations of nozzle tip and nozzle actuator are possible.

In advantageous embodiments, the actuating means are electrically- or pneumatically-controlled actuators, which are operably linked to the fixed nozzles, and function by allowing rapid cycling between open (i.e. permitting fluid flow to the nozzle) and closed (i.e. blocking fluid flow to the nozzle) positions.

In an embodiment, the automatic spray nozzles are in fluid connection with pressurized fluid, which is supplied from a fluid reservoir. The automatic spray nozzles may be turned on or off, so as to minimize the amount of fluid that is required to vaccinate and/or administer probiotics to the avian animals. In some embodiments, the automatic spray nozzles are capable of rapid cycling, opening and closing up to or in excess of at least 10,000 times per second. In some embodiments, the cycling may exceed 15,000 times per second.

In an embodiment, the automatic spray nozzles may be rapidly turned on and off to suit any field conditions. For example, the automatic spray nozzles may be turned off in between chick-containing baskets, to reduce wasted fluid. In another embodiment, if the conveyor belt is moving the chicks relatively slowly, it may be desirable for the nozzles to deliver bursts of fluid droplets, rather than constantly stream the fluid droplets. Accordingly, by equipping the apparatus with nozzles capable of rapidly cycling between their on and off positions, it is possible to deliver any amount of fluid per unit time to accommodate any field conditions.

In a particular embodiment, the instant disclosure provides an improved inline spray applicator having electrically- or pneumatically-actuated spray nozzles. The apparatus may comprise a Pulse Width Modulation (PWM) controller with electrically actuatable nozzles (e.g. Pulsa-Jet® or AA250AUH nozzles) from Spraying Systems Co. The PWM technology allows the inline spray applicator nozzles to switch on and off very quickly to control flow rate, thus providing a wide range of flow rates at constant pressure, spray angle, and droplet size.

In some embodiments, the spray applicator comprises a Precision Spray Control (PSC), which comprises a PulsaJet® automatic spray nozzles and an AutoJet® spray controller. Many systems also include a spray manifold. With PSC, the AutoJet spray controller turns electrically-actuated PulsaJet nozzles on and off very quickly to control flow rate. The cycling may be so fast that the flow often appears to be constant. Flow rate may be adjusted automatically based on changes in operating conditions such a variations in line speed. Flow rate adjustments occur almost instantaneously to ensure the proper application rate.

In some embodiments, electrically-actuated hydraulic spray nozzles can achieve significantly low flow rates, which may be comparable to the flow rates of air atomizing nozzles.

In an advantageous embodiment, flow rate is changed by modifying the nozzle duty cycle and cycling frequency, not by changing pressure. This feature of the spray applicator is particularly useful in hatcheries, since conveyor speeds vary from hatchery to hatchery. In a particularly advantageous embodiment, the spray applicator may be operated at a constant pressure during a given vaccination run or during administration of probiotics to the avian animal.

In an embodiment, the spray applicator is free-standing and adaptable to any conveyor belt system. Baskets or crates may be moved continuously, irrespective of conveyor belt speed, to reduce vaccination or administration time. The spray applicator may comprise a dosage setting means, which allows a user to select from a range of possible dose volumes. For example, the volume may be from about 5 mL to about 25 mL.

In another embodiment, the spray applicator may be equipped with an alarm system, to notify users of blocked baskets/crates or empty liquid reservoirs/tanks. The spray applicator may be controlled by any suitable user interface, including a user-friendly tactile screen. In particularly embodiments, the spray applicator collects and stores data, which may be downloaded to a suitable storage means, including a USB-compliant device, to enable traceability.

In some embodiments, the spray applicator comprises an AutoJet Model 1550+ Modular Spray System.

In an embodiment, the spray applicator comprises a means for cleansing to ensure good hygienic conditions.

In an embodiment, the spray applicator comprises an interface that may allow a user to select from at least three different timing modes: a fixed spray time (e.g. FIG. 11A); a variable spray time (e.g. FIG. 11B); and "repeat" (e.g. FIG. 11C). Moreover, the interface may allow the user to enter start delay(s) and stop delay(s) to adapt the spray applicator to different hatchery chick boxes to ensure accurate placement and minimal vaccine or probiotic waste.

In an advantageous embodiment, the spray applicator comprises automatic spray nozzles and employs pressures to achieve an ideal target droplet size. In an embodiment, the target droplet size is about 125 to about 300 microns. In another embodiment, the target droplet size is about 150, 200, or 250 microns. Now that the invention has been disclosed, the skilled person will instantly appreciate a wide range of effective combinations of pressure and automatic spray nozzle combinations.

In another embodiment, using the inline spray applicator of the invention for administering probiotics enables a predetermined dose of liquid or liquid-like gel probiotic to be sprayed directly onto the birds. It is expected that as the birds preen they will ingest the probiotics from their feathers. It is known that larger droplet sizes are more suited for ingestion, while smaller droplet sizes are more suitable for administration of vaccines that are intended to be inhaled.

In another embodiment, the probiotic formulation may be in the form of a liquid-like gel. A "liquid-like gel" as used herein is a gel that is easily disrupted or thinned, and that liquefies or becomes less gel-like and more liquid-like under stress, such as caused by the gel being pumped through the spray applicator, but which quickly returns to a gel when the movement or other stress is alleviated or removed, such as when movement of the fluid exiting the spray applicator is stopped, as for example when the exiting fluid lands on the targeted chick or chick crate. The skilled person knows how to make a formulation more the gel-like or liquid-like by adjusting the amount of gelling agent used in the formulation. One type of liquid-like gel suitable for use in delivering probiotics to birds or chicks is disclosed in Wright et al, PCT patent publication number WO2001095891. Other suitable liquid-like gels for use to deliver probiotics to birds or chicks include GroGel™ by MS BioScience of Madison, Wis., and Gel-Pac™ Animal Science Products, Inc. PO Drawer 631408 Nacogdoches, TX.

In another embodiment, the liquid-like gel may pass through the automatic spray nozzles and thereby be dispersed from the spray applicator in the form of small gel beadlets. The term "beadlet" as used herein refers to small discrete particles, which have a mean particle size from about 125 to about 300 microns in diameter and are usually nearly spherical. Beadlets contain one or more probiotics in an encapsulated form.

As used above, and throughout the description of the invention, the following terms, unless otherwise indicated, shall be understood to have the following meanings:

The term "and/or" as used herein includes any and all combinations of one or more of the associated listed items.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "effective amount" as used herein means an amount of a composition according to the present invention effective in producing the desired veterinary effect.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. This invention includes all modifications and equivalents of the subject matter recited in the aspects or claims presented herein to the maximum extent permitted by applicable law. Accordingly, it is an object of the invention to not encompass within the invention any previously known product, process of making the product, or method of using the product such that Applicant reserves the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicant reserves the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may be best understood in conjunction with the accompanying drawings, in which.

DETAILED DESCRIPTION

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

In an embodiment, the apparatus comprises an inline spray applicator system, comprising a modular spray system, comprising one or more rapidly actuating automatic spray nozzles.

Figure 11A:
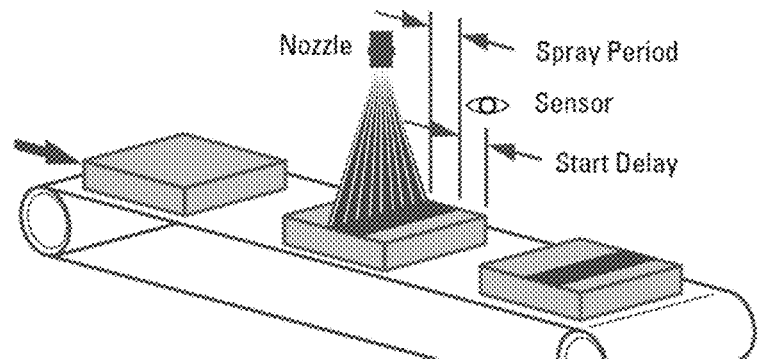
FIG. 11A provide a schematic example of a fixed spray time.
Figure 11B:
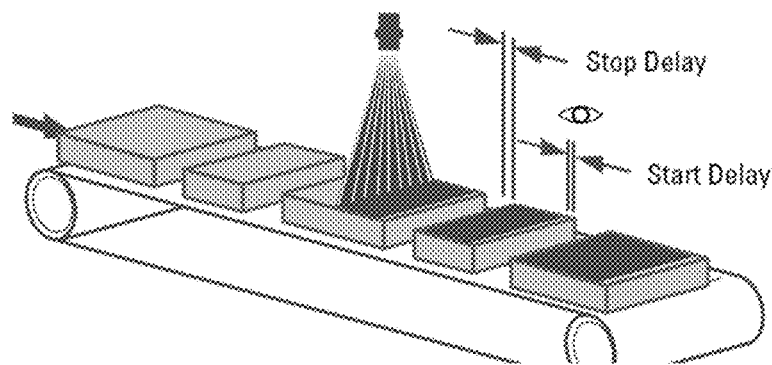
FIG. 11B provides a schematic example of a variable spray time.
Figure 11C:
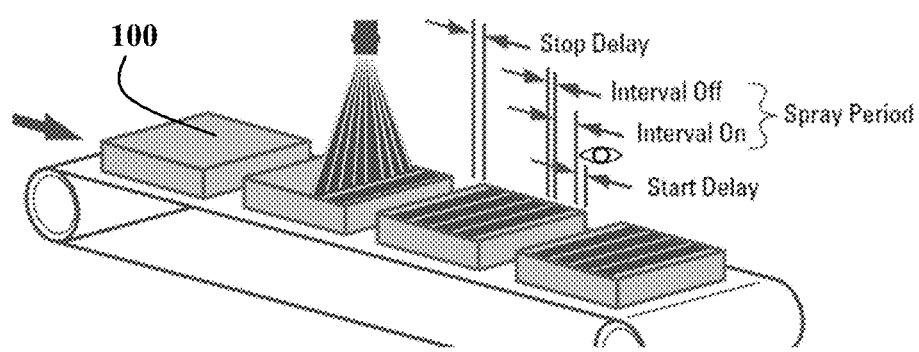
FIG. 11C provides a schematic example of a "repeat"

In an embodiment, the apparatus may be programmed such that the nozzles operate in a "fixed spray time" mode. In this mode, the nozzle(s) will spray once after it is triggered based on entered start delay and spray period, then stops spraying until next trigger signal (FIG. 11A).

In another embodiment, the apparatus may be programmed such that the nozzles operate in a "variable spray time" mode. This timing mode creates spray periods of variable lengths. The apparatus will spray following a trigger, and the spray period is based on the sensor "seeing" (or otherwise detecting) the object then utilizing the programmed start delay and stop delay. The length of the spray depends on the length of the trigger input.

In another embodiment, the apparatus may be programmed such that the nozzles operate in a "repeat" mode. This timing mode creates a continuous repetition of spray applications for a variable time or spray period based on object size. The system will spray following the trigger, spray period is based on the sensor seeing the object then utilizing the entered timing settings, spray delay, interval on, interval off, repeats these until trigger off signal then incorporates stop delay.

In an advantageous embodiment, the spray applicator is equipped with an AutoJet 1550-plus Modular Spray System (Spraying Systems Co.). Spraying Systems' 2013 "Bulletin No. 626D" is incorporated herein by reference in its entirety.

In an embodiment, the Modular Spray System conforms to the following parameters:
Power required: 110 VAC, 60 Hz, 15 A, 1 Ø (capable to 260 VAC, 50 Hz, 15 A, 1 Ø)
Control panel: NEMA 4 with door closed (stainless steel);
Air inlet shut-off/lockout and filter assembly;
Optional air operated double diaphragm pump;
Liquid outlet strainer 100 mesh;
Liquid pressure regulator and gauge;
Control valve for recirculation to tank; (pump and pumpless versions)
Standard triggering options: trigger cable, photoelectric sensor, thru-beam, hand pendant
Controls up to eight automatic spray nozzles (varies by type)
Dimensions: approximately 29" (0.75 m) tall, 14" (0.36 m) wide and weighs less than 58 lbs. (26.3 kg).

In an embodiment, any suitable high pressure pumping system can be used in the practice of the invention, including the AutoJet system, which is manufactured by Spraying Systems, Inc. (Chicago, Ill.). The fluid, vaccine and/or probiotic formulation may be pumped using a hydraulic liquid pump at pressures from about 30 psi to about 100 psi through a fluid jet nozzle tips such as, but not limited to 8001E or 6501E (Spraying Systems, Chicago, Ill.).

The designation on the TeeJet® nozzle tips has a specific meaning. The first two numbers indicate the spray angle. An 8001 nozzle tip has an 80 degree spray angle at 40 psi. The second two numbers indicate the capacity of the nozzle tip. An 8001 nozzle tip would deliver 0.1 gallons per minute (gpm) of water at 40 pounds per square inch pressure (psi). The "E" following the numbers means that the nozzle tip is an even spray nozzle and can be used for banding. As an example of another manufacturer, the Delavan nozzle tip that is equivalent to the 8001E Teejet nozzle tip is the LE-1 80°. Compatible nozzles are thus envisioned by the inventor. Accordingly, a 6501E nozzle tip has a 65 degree spray angle at 40 psi, and would deliver about 0.1 gpm of water at 40 psi.

When two or more automatic spray nozzles are used, the nozzles generally spray towards one another at approximately 45° from vertical. The automatic spray nozzles may be arranged over the row rather than at the sides of the row.

In an aspect, the invention provides an automated inline spray applicator comprising a housing, at least one rapidly actuatable automatic spray nozzle, and, a programmable spray module. The programmable spray module (PSM) may be in electrical, pneumatic or hydraulic connection with the at least one automatic spray nozzle, and the spray nozzle may be in fluid communication with a fluid reservoir/tank. A separate source of pressurized air may be employed to supply the pressure required to deliver the fluid to and through the nozzle tips, and the pressurized air may be in fluid communication with both the tank and the automatic spray nozzles. The spray module is configured to receive user inputs to control all aspects of nozzle functioning, including controlling the amount and timing of fluid that flows from the tank, through the applicator conduits, and ultimately, out through the nozzles. An advantageous spray module is the AutoJet Model 1550+ Modular Spray System, manufactured by Spraying Systems. The 1550 is a self-contained automated spray system that comprises everything needed for a user to operate automatic spray nozzles, including the automatic spray nozzles described in this application.

In some embodiments, automated spray control ensures precision and accurate placement of the sprayed liquid with minimal waste. Further, automatic control provides proper flow and droplet size, and eliminates uneven application of the sprayed liquids. In an advantageous embodiment, the automated control is provided by Precision Spray Control (PSC) with electrically-actuated PulsaJet® and AA250AUH automatic spray nozzles. PSC is a versatile automatic spray system, which is configured to operate both electrically- and pneumatically-actuated automatic spray nozzles.

In some embodiments, the inline spray applicator, comprises an 8001E, an 6501E or another suitable nozzle tip, which is capable of producing droplets sized from about 125 to about 300 microns, particularly about 150 microns, from fluid pressurized from about 30 psi to about 80 psi.

In some embodiments, the inline spray applicator comprises a base, which comprises a rolling means, for facilitating the movement of the apparatus from one location to another location. The base may also comprise a rolling means locking means, for reversibly preventing the rolling means from rolling. The locking means may be any suitable brake or lock, including mechanical and magnetic brakes or locks. Suitable locks/brakes include those used on known swivel casters, which easily transition between stationary stability and mobility. The use of well-known floor locks is also envisioned.

In some embodiments, the base may comprise a standing means, for maintaining the applicator in a fixed position when movement of the applicator is not desired.

In some embodiments, the spray applicator housing may be attached to and supported by the base, and the housing may comprise a tank holder for holding a tank.

In some embodiments, the tank comprises a lid optionally comprising a safety blow off valve. Moreover, the tank is in fluid communication with a programmable spray module, which is itself in electrical or pneumatic communication with one or a plurality of actuatable automatic spray nozzles.

In some embodiments, the automatic spray nozzles are electrically connected to the spray module via suitable electrical connectors including wires. The wires and fluid conduits may pass through the housing via an orifice.

In some embodiments, the tank further comprises a level liquid float, for determining the level of fluid in the tank.

In some embodiments, the flow of fluid may be functionally connected to a sensor, which is capable of relaying/communicating a fluid flow status to a user via the spray module or via a light indicator.

In some embodiments, the applicator may comprise a source of pressurized air for supplying pressure to the fluid prior to its entry into the spray nozzles. For example, the applicator may comprise an air tank and compressor, which are configured to pressurize the fluid contained within the reservoir/tank. The pressure source is thus in fluid communication with the fluid that is delivered to the automatic spray nozzles, for administration to the young avian animals.

In some embodiments, the housing is configured to be connected to a vertical nozzle hood assembly adjustment rod via a rod attachment means. The vertical nozzle hood assembly adjustment rod is configured to be connected to a horizontal rod, which is configured to connect to hood panels. The hood panels are configured to connect to the horizontal rod via suitable hood panel attachment means. In some embodiments, the hood panel attachment means is a hood mounting plate, which has slots for receiving corresponding panel components. The adjustment rods allow the automatic spray nozzles to be optimally positioned above conveyor systems having different sizes. For example, the hood panels can be positioned higher or lower (by varying the vertical position along the vertical rod) for use in hatcheries using relatively higher or lower conveyor systems. Similarly, the automatic spray nozzles can be variably positioned along the horizontal rod for use in hatcheries using wider or more narrow conveyor systems.

In some embodiments, the spray applicator comprises a vaccine or other fluid alarm status indicator light tower and a pressure regulator, situated at a top-most portion of the housing.

In some embodiments, the inline spray applicator comprises a pressure gauge indicator and an access hatch, wherein the hatch provides secure access to the programmable spray module. The spray module is generally operable and programmable via a touch screen.

In some embodiments, the spray applicator of claim comprises an "on" indicator and an "on/off" switching means.

In a particular embodiment, the spray applicator comprises:
a. a base comprising a rolling means, a rolling-blocking means, and a standing means;
b. a housing, attached to and supported by the base, and comprising a tank holder, a hatch, a light tower indicator, a pressure regulator, an orifice through which electrical wires and fluid conduits may pass, at least one rapidly actuatable automatic spray nozzle in fluid connection with the tank;
c. a vertical rod attached to the housing via an attachment means, and also attached to a horizontal rod via one or more panel attachment means; and
wherein the automatic spray nozzle(s) is(are) connected to the horizontal rod; and,
wherein the housing contains a programmable spray module.

In another aspect, the invention provides a method for vaccinating young avian animals, including day-old chicks, comprising administering vaccine using a spray applicator as described herein. For administration, the spray applicator is generally moved into position above the animals to be vaccinated, which are generally contained within crates/baskets, which crates/baskets are being transported along a conveyor belt (see e.g. FIG. 1F).

In some embodiments of the method, greater than 90% of the vaccine droplets have diameters from about 125 to about 300 microns.

In other embodiments, the control module is programmed to cause the automatic spray nozzles to stop and start to accommodate different sized chick crates/baskets. In still other embodiments, the module is programmed to direct the automatic spray nozzles to stop and start to accommodate different conveyer rates. Any combination of chick crate/basket size and conveyor rate can be accommodated by programming the module to actuate the automatic nozzles to cycle between open (i.e. fluid may pass through the nozzle tip) and closed (i.e. fluid may not pass through the nozzle tip) positions.

In some embodiments, the invention provides a method of treating young avian animals, including day-old chicks, with a probiotic formulation, comprising the steps of dispersing the probiotic formulation using a spray applicator as described herein; and, allowing the chicks to consume the dispensed probiotic formulation, thereby treating the young avian animals with a probiotic formulation.

In some embodiments, the probiotic formulation may be a liquid or liquid-like gel.

The invention is further illustrated by the following non-limiting examples.

EXAMPLES

Example 1

Evaluation of TPU VeeJet® Nozzle Tips for their Suitability in Producing Droplet Sizes Appropriate for Use in Spray Vaccination or Delivery of Probiotic Formulations Nine (9) samples of various 80° and 95° TPU VeeJet® Nozzle tips (capacities indicated below) were submitted for testing of drop size, with the objective of reporting the pressures required for achieving the target volume median diameters of 150, 200 and 250 microns. In the final analysis, $D_{V0.10}$ and $D_{V0.90}$ values would be compared to see the difference (if any) between the standard TPU tips and even (E) tips. Moreover, the 65° version of each capacity was estimated. For the capacities tested, the Sympatec analyzer was used to measure drop size using a nozzle-laser distance of 6-inches. The spray was fully developed at this distance. For each condition, the nozzle was sprayed horizontally and the entire spray was measured. Three (3) measurements were taken, averaged and reported below. Table 1 summarizes the pressures required to achieve the target volume median diameters of 150, 200 and 250 microns for each indicated TPU VeeJet® nozzle. A single average of three (3) drop size runs as well as the average flow rate for each pressure was included.

The drop size terminology used throughout this application is in accordance with ASTM® standard E1620-97, and is defined with more detailed information in Bulletin 459c: Understanding Drop Size, (please see the following web location: hypertext transfer protocol://service. spray.com/lit/view_lit.asp?code=B459C).

TABLE 1

Drop size diameter and flow rate as a function of Nozzle tip type and Pressure (the values reported here are for water; other fluids may yield different values)

| Nozzle Tip | Pressure (PSI) | Flow Rate (GPM) | Target $D_{V0.50}$ | Estimated Drop Size Diameters (microns) | | |
|---|---|---|---|---|---|---|
| | | | | $D_{V0.10}$ | $D_{V0.50}$ | $D_{V0.90}$ |
| 8001 | 32.5 | 0.0916 | 150 | 64 | 150 | 280 |
| | 17.5 | 0.0675 | 200 | 83 | 198 | 346 |
| | 12.0 | 0.0564 | 250 | 101 | 249 | 416 |

TABLE 1-continued

Drop size diameter and flow rate as a function of Nozzle tip type and Pressure (the values reported here are for water; other fluids may yield different values)

| Nozzle Tip | Pressure (PSI) | Flow Rate (GPM) | Target $D_{V0.50}$ | Estimated Drop Size Diameters (microns) | | |
|---|---|---|---|---|---|---|
| | | | | $D_{V0.10}$ | $D_{V0.50}$ | $D_{V0.90}$ |
| 8002 | 81.5 | 0.2843 | 150 | 57 | 150 | 301 |
| | 41.4 | 0.2033 | 200 | 75 | 196 | 356 |
| | 22.8 | 0.1513 | 250 | 98 | 248 | 409 |
| 8003 | 150.5 | 0.5743 | 150 | 54 | 152 | 346 |
| | 73.1 | 0.4014 | 200 | 68 | 199 | 394 |
| | 40.4 | 0.2997 | 250 | 88 | 249 | 446 |
| 8001E | 32.5 | 0.0899 | 150 | 60 | 150 | 328 |
| | 20.7 | 0.0720 | 200 | 76 | 201 | 398 |
| | 15.6 | 0.0631 | 250 | 89 | 248 | 451 |
| 8002E | 154.8 | 0.3897 | 150 | 50 | 150 | 307 |
| | 75.5 | 0.2730 | 200 | 66 | 199 | 368 |
| | 34.5 | 0.1849 | 250 | 80 | 250 | 433 |
| 8003E | 206.1 | 0.6722 | 150 | 46 | 149 | 321 |
| | 116.0 | 0.5058 | 200 | 65 | 201 | 387 |
| | 61.4 | 0.3688 | 250 | 83 | 249 | 443 |
| 9501E | 27.5 | 0.0840 | 150 | 60 | 149 | 346 |
| | 17.5 | 0.0672 | 200 | 75 | 198 | 422 |
| | 13.8 | 0.0601 | 250 | 89 | 249 | 461 |
| 9502E | 111.5 | 0.3376 | 150 | 54 | 151 | 306 |
| | 51.3 | 0.2295 | 200 | 68 | 199 | 376 |
| | 24.3 | 0.1586 | 250 | 86 | 249 | 432 |
| 9503E | 167.1 | 0.6125 | 150 | 48 | 151 | 318 |
| | 83.2 | 0.4336 | 200 | 65 | 200 | 387 |
| | 41.2 | 0.3063 | 250 | 81 | 251 | 451 |

TABLE 2

Drop size diameter and flow rate as a function of Nozzle tip type and Pressure (65° nozzle angle; fluid is water)

| Nozzle Tip | Pressure (PSI) | Flow Rate (GPM) | Target $D_{V0.50}$ | Estimated Drop Size Diameters (microns) | | |
|---|---|---|---|---|---|---|
| | | | | $D_{V0.10}$ | $D_{V0.50}$ | $D_{V0.90}$ |
| 6501 | 38.1 | 0.098 | 150 | 64 | 150 | 280 |
| | 20.7 | 0.072 | 200 | 83 | 198 | 346 |
| | 14.0 | 0.059 | 250 | 101 | 249 | 416 |
| 6502 | 103.9 | 0.322 | 150 | 57 | 150 | 301 |
| | 55.6 | 0.236 | 200 | 75 | 196 | 356 |
| | 29.9 | 0.173 | 250 | 98 | 248 | 409 |
| 6503 | 173.8 | 0.625 | 150 | 54 | 152 | 346 |
| | 93.5 | 0.459 | 200 | 68 | 199 | 394 |
| | 54.6 | 0.350 | 250 | 88 | 249 | 446 |
| 6501E | 36.7 | 0.096 | 150 | 60 | 150 | 328 |
| | 23.6 | 0.077 | 200 | 76 | 201 | 398 |
| | 17.5 | 0.066 | 250 | 89 | 248 | 451 |
| 6502E | 195.2 | 0.442 | 150 | 50 | 150 | 307 |
| | 100.2 | 0.317 | 200 | 66 | 199 | 368 |
| | 44.6 | 0.211 | 250 | 80 | 250 | 433 |
| 6503E | 238.1 | 0.732 | 150 | 46 | 149 | 321 |
| | 148.5 | 0.578 | 200 | 65 | 201 | 387 |
| | 82.7 | 0.431 | 250 | 83 | 249 | 443 |

Example 2

Evaluation of Single Nozzle (Different Nozzles at Fixed Pressures)

TABLE 3

Dose volume vs. Time. One nozzle tip test; 150 μM; Nozzle tip 8001E @ 32.5 psi

|   | Dose (mL) delivered during 0.5 seconds | Dose (mL) delivered during 3 seconds |
|---|---|---|
| 1 | 2.738 | 16.37 |
| 2 | 2.734 | 16.37 |
| 3 | 2.725 | 16.38 |
| 4 | 2.723 | 16.38 |
| 5 | 2.725 | 16.39 |
| 6 | 2.721 | 16.37 |
| 7 | 2.723 | 16.38 |
| 8 | 2.726 | 16.38 |
| 9 | 2.725 | 16.38 |
| 10 | 2.726 | 16.37 |
| Average | 2.727 | 16.38 |

TABLE 4

Spray distribution test. 7 mL of water was delivered via 30 shots, from nozzle tip 8001E @ 32.5 psi, to a typical poultry basket, containing 66 collection cups. Volume delivered to each cup

| | | | | |
|---|---|---|---|---|
| 1.88 | 2.077 | 2.205 | 2.128 | 1.87 |
| 1.919 | 1.946 | 2.295 | 2.214 | 2.188 |
| 1.661 | 1.531 | 1.986 | 2.169 | 2.063 |
| 1.542 | 1.577 | 1.894 | 2.066 | 1.868 |
| 1.602 | 1.836 | 1.569 | 1.832 | 1.189 |
| 1.886 | 2.152 | 1.826 | 1.567 | 1.186 |
| 1.957 | 2.073 | 2.174 | 1.678 | 1.185 |
| 2.07 | 1.518 | 2.23 | 2.021 | 1.588 |
| 1.95 | 1.702 | 2.155 | 2.131 | 1.73 |
| 1.712 | 2.029 | 2.028 | 2.118 | 1.425 |
| 1.537 | 2.147 | 2.057 | 1.878 | |
| 1.867 | 1.949 | 1.833 | 1.792 | |
| 2.059 | 1.521 | 1.583 | 1.51 | |
| 2.149 | 1.642 | 1.734 | 1.527 | |

TABLE 5

Dosage test (spray period of 1.2 seconds)

| | |
|---|---|
| 1 | 7.268 |
| 2 | 7.253 |
| 3 | 7.226 |
| 4 | 7.224 |
| 5 | 7.211 |
| 6 | 7.215 |
| 7 | 7.211 |
| 8 | 7.236 |
| 9 | 7.207 |
| 10 | 7.214 |
| 11 | 7.177 |
| 12 | 7.178 |
| 13 | 7.173 |
| 14 | 7.177 |
| 15 | 7.175 |
| 16 | 7.161 |
| 17 | 7.174 |
| 18 | 7.172 |
| 19 | 7.172 |
| 20 | 7.175 |
| 21 | 7.164 |
| 22 | 7.166 |
| 23 | 7.186 |
| 24 | 7.196 |
| 25 | 7.18 |
| 26 | 7.19 |
| 27 | 7.174 |
| 28 | 7.172 |
| 29 | 7.173 |
| 30 | 7.179 |
| 31 | 7.186 |
| 32 | 7.183 |
| 33 | 7.183 |
| 34 | 7.178 |
| 35 | 7.179 |
| 36 | 7.179 |
| 37 | 7.185 |
| 38 | 7.182 |
| 39 | 7.177 |
| 40 | 7.175 |
| 41 | 7.179 |
| 42 | 7.185 |
| 43 | 7.183 |
| 44 | 7.189 |
| 45 | 7.166 |
| 46 | 7.23 |
| 47 | 7.224 |
| 48 | 7.216 |
| 49 | 7.22 |
| 50 | 7.269 |
| 51 | 7.256 |
| 52 | 7.248 |
| 53 | 7.231 |
| 54 | 7.216 |
| 55 | 7.197 |
| 56 | 7.172 |
| 57 | 7.158 |
| 58 | 7.156 |
| 59 | 7.219 |
| 60 | 7.211 |
| 61 | 7.188 |
| 62 | 7.18 |
| 63 | 7.188 |
| 64 | 7.183 |
| 65 | 7.205 |
| 66 | 7.198 |
| 67 | 7.183 |
| 68 | 7.18 |
| 69 | 7.18 |
| 70 | 7.174 |
| 71 | 7.173 |
| 72 | 7.175 |
| 73 | 7.171 |
| 74 | 7.197 |
| 75 | 7.188 |
| 76 | 7.202 |
| 77 | 7.203 |
| 78 | 7.197 |
| 79 | 7.208 |
| 80 | 7.186 |
| 81 | 7.162 |
| 82 | 7.16 |
| 83 | 7.15 |
| 84 | 7.155 |
| 85 | 7.147 |
| 86 | 7.147 |
| 87 | 7.161 |
| 88 | 7.162 |
| 89 | 7.153 |
| 90 | 7.161 |
| 91 | 7.18 |
| 92 | 7.174 |
| 93 | 7.185 |
| 94 | 7.177 |
| 95 | 7.175 |
| 96 | 7.179 |
| 97 | 7.164 |
| 98 | 7.177 |
| 99 | 7.179 |
| 100 | 7.18 |

TABLE 6

Dose (g) volume vs. Time. One nozzle tip test; 200 μM; Nozzle tip 9502E @ 51.5 psi

| | Dose (mL) delivered during 0.5 seconds | Dose (mL) delivered during 3 seconds |
|---|---|---|
| 1 | 6.564 | 39.106 |
| 2 | 6.542 | 39.159 |
| 3 | 6.565 | 39.097 |
| 4 | 6.555 | 39.13 |
| 5 | 6.541 | 39.109 |
| 6 | 6.54 | 39.092 |
| 7 | 6.511 | 39.111 |
| 8 | 6.5 | 39.15 |
| 9 | 6.496 | 39.158 |
| 10 | 6.498 | 39.16 |
| Average | 6.5312 | 39.1272 |

TABLE 7

Dosage test (spray period of 1.1 seconds)

| | |
|---|---|
| 1 | 14.365 |
| 2 | 14.369 |
| 3 | 14.355 |
| 4 | 14.335 |
| 5 | 14.361 |
| 6 | 14.384 |
| 7 | 14.376 |
| 8 | 14.348 |
| 9 | 14.385 |
| 10 | 14.373 |
| 11 | 14.349 |
| 12 | 14.354 |
| 13 | 14.351 |
| 14 | 14.352 |
| 15 | 14.365 |
| 16 | 14.357 |
| 17 | 14.313 |
| 18 | 14.362 |
| 19 | 14.381 |
| 20 | 14.357 |
| 21 | 14.318 |
| 22 | 14.29 |
| 23 | 14.277 |
| 24 | 14.315 |
| 25 | 14.326 |
| 26 | 14.276 |
| 27 | 14.295 |
| 28 | 14.283 |
| 29 | 14.277 |
| 30 | 14.284 |
| 31 | 14.276 |
| 32 | 14.265 |
| 33 | 14.269 |
| 34 | 14.258 |
| 35 | 14.263 |
| 36 | 14.309 |
| 37 | 14.295 |
| 38 | 14.294 |
| 39 | 14.289 |
| 40 | 14.311 |
| 41 | 14.309 |
| 42 | 14.262 |
| 43 | 14.321 |
| 44 | 14.33 |
| 45 | 14.329 |
| 46 | 14.3 |
| 47 | 14.314 |
| 48 | 14.291 |
| 49 | 14.307 |
| 50 | 14.313 |
| 51 | 14.317 |
| 52 | 14.317 |
| 53 | 14.315 |
| 54 | 14.309 |
| 55 | 14.319 |
| 56 | 14.332 |
| 57 | 14.311 |
| 58 | 14.301 |
| 59 | 14.25 |
| 60 | 14.255 |
| 61 | 14.224 |
| 62 | 14.283 |
| 63 | 14.321 |
| 64 | 14.343 |
| 65 | 14.338 |
| 66 | 14.328 |
| 67 | 14.328 |
| 68 | 14.336 |
| 69 | 14.363 |
| 70 | 14.334 |
| 71 | 14.309 |
| 72 | 14.314 |
| 73 | 14.242 |
| 74 | 14.234 |
| 75 | 14.315 |
| 76 | 14.322 |
| 77 | 14.315 |
| 78 | 14.301 |
| 79 | 14.302 |
| 80 | 14.303 |
| 81 | 14.345 |
| 82 | 14.332 |
| 83 | 14.314 |
| 84 | 14.312 |
| 85 | 14.323 |
| 86 | 14.334 |
| 87 | 14.323 |
| 88 | 14.323 |
| 89 | 14.326 |
| 90 | 14.326 |
| 91 | 14.312 |
| 92 | 14.264 |
| 93 | 14.236 |
| 94 | 14.221 |
| 95 | 14.219 |
| 96 | 14.228 |
| 97 | 14.246 |
| 98 | 14.234 |
| 99 | 14.232 |
| 100 | 14.238 |

TABLE 8

Dose (g) volume vs. Time. One nozzle tip test; 250 μM; Nozzle tip 8003E @ 61.4 psi

| | Dose (mL) delivered during 0.5 seconds | Dose (mL) delivered during 3 seconds |
|---|---|---|
| 1 | 10.217 | 61.256 |
| 2 | 10.242 | — |
| 3 | 10.203 | — |
| 4 | 10.224 | — |
| 5 | 10.204 | — |
| 6 | 10.22 | — |
| 7 | 10.227 | — |
| 8 | 10.26 | — |
| 9 | 10.272 | — |
| 10 | 10.268 | — |
| Average | 10.2337 | 61.256 |

Example 3

Two Nozzles Test

TABLE 9

Dose (g) volume vs. Time. One nozzle tip test; 150 μM;
Two 6501E nozzle tips @ 36.7 psi

|  | Dose (mL) delivered during 0.5 seconds | Dose (mL) delivered during 3 seconds |
|---|---|---|
| 1 | 5.914 | 35.097 |
| 2 | 5.912 | 35.167 |
| 3 | 5.905 | 35.154 |
| 4 | 5.901 | 35.125 |
| 5 | 5.892 | 35.109 |
| 6 | 5.889 | 35.104 |
| 7 | 5.88 | 35.132 |
| 8 | 5.868 | 35.117 |
| 9 | 5.872 | 35.08 |
| 10 | 5.863 | 35.144 |
| Average | 5.8896 | 35.1229 |

TABLE 10

Dose (g) volume vs. Time. One nozzle tip test; 200 μM;
Two 6502E nozzle tips @ 55.6 psi

|  | Dose (mL) delivered during 0.5 seconds | Dose (mL) delivered during 3 seconds |
|---|---|---|
| 1 | 12.918 | 76.678 |
| 2 | 12.908 | — |
| 3 | 12.895 | — |
| 4 | 12.83 | — |
| 5 | 12.803 | — |
| 6 | 12.777 | — |
| 7 | 12.776 | — |
| 8 | 12.767 | — |
| 9 | 12.768 | — |
| 10 | 12.787 | — |
| Average | 12.8229 | 76.678 |

TABLE 11

Dose (g) volume vs. Time. One nozzle test; 250 μM;
Two 6503E nozzles @ 54.6 psi

|  | Dose (mL) delivered during 0.5 seconds | Dose (mL) delivered during 3 seconds |
|---|---|---|
| 1 | 18.559 | 111.484 |
| 2 | 18.572 | — |
| 3 | 18.571 | — |
| 4 | 18.567 | — |
| 5 | 18.561 | — |
| 6 | 18.547 | — |
| 7 | 18.558 | — |
| 8 | 18.578 | — |
| 9 | 18.585 | — |
| 10 | 18.561 | — |
| Average | 18.5659 | 111.484 |

Figure 12:
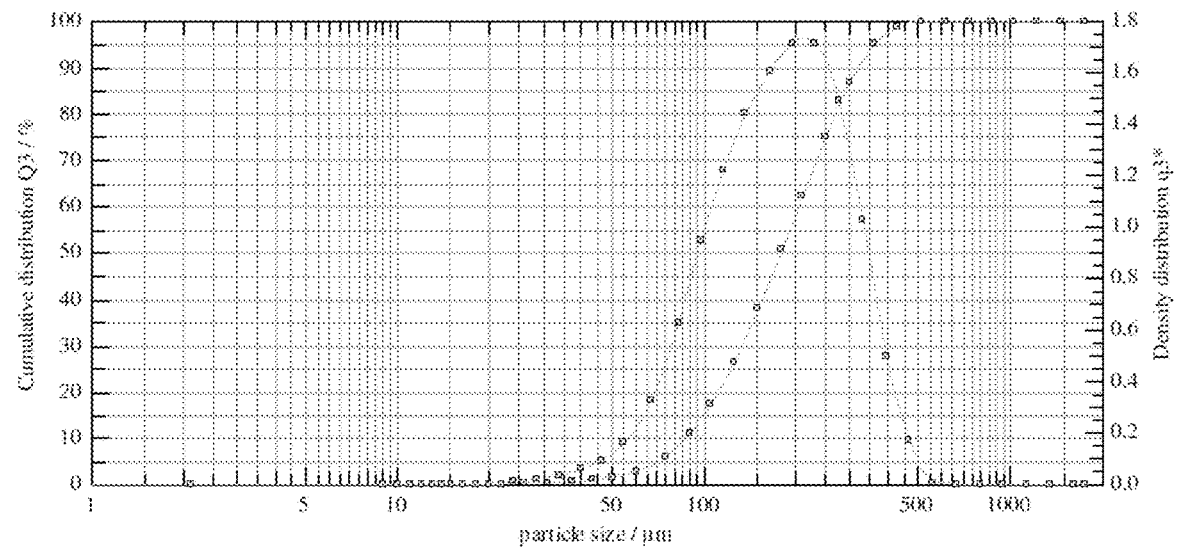
FIG. 12 is a graph of the cumulative and density distributions of droplet sizes produced by the TPU 8001 nozzle tip at 30 psi. TPU flat nozzle tips yield a high impact solid stream or flat spray pattern with spray angles of 0° (solid stream) to 110°.

Data underlying FIG. 12: Height: 9.5 Nozzle: TPU—8001; Pressure: 30 psi; Copt=3.67% (all the data below and presented graphically in FIGS. 12-17 were evaluated using "WINDOX 5.6.1.0, FREE" software.
HELOS (H2476) & SPRAYER, R6: 0.5/9.0 . . . 1750 μm
Volume Median Diameter: $D_{V0.5}$ 178.80 μm
Number Median Diameter: $D_{N0.5}$ 62.62 μm; $D_{V0.1}$ 87.35 μm; $D_{V0.9}$ 323.89 $D_{V0.99}$ 446.91 μm
Relative Span Factor: RSF 1.32
Arithmetic Mean Diameter: $D_{10}$ 75.43 μm
Surface Mean Diameter: $D_{20}$ 90.50 μm
Volume Mean Diameter: $D_{30}$ 106.97 μm
Surface-Dia. Mean Diameter: $D_{21}$ 108.59 μm
Evaporative Mean Diameter: $D_{31}$ 127.38 μm
Sauter Mean Diameter: $D_{32}$ 149.42 μm

TABLE 12

Cumulative Distribution data underlying the graph in FIG. 12

| Diameter (μm) | Volume (%) |
|---|---|
| 9.00 | 0.00 |
| 11.00 | 0.00 |
| 13.00 | 0.00 |
| 15.00 | 0.00 |
| 18.00 | 0.00 |
| 22.00 | 0.00 |
| 26.00 | 0.08 |
| 31.00 | 0.24 |
| 37.00 | 0.51 |
| 43.00 | 0.89 |
| 50.00 | 1.49 |
| 60.00 | 2.76 |
| 75.00 | 5.92 |
| 90.00 | 10.89 |
| 105.00 | 17.21 |
| 125.00 | 26.40 |
| 150.00 | 37.79 |
| 180.00 | 50.51 |
| 210.00 | 61.97 |
| 250.00 | 74.95 |
| 300.00 | 86.76 |
| 360.00 | 94.90 |
| 430.00 | 98.72 |
| 510.00 | 99.95 |
| 610.00 | 100.00 |
| 730.00 | 100.00 |
| 870.00 | 100.00 |
| 1030.00 | 100.00 |
| 1230.00 | 100.00 |
| 1470.00 | 100.00 |
| 1750.00 | 100.00 |

Figure 13:
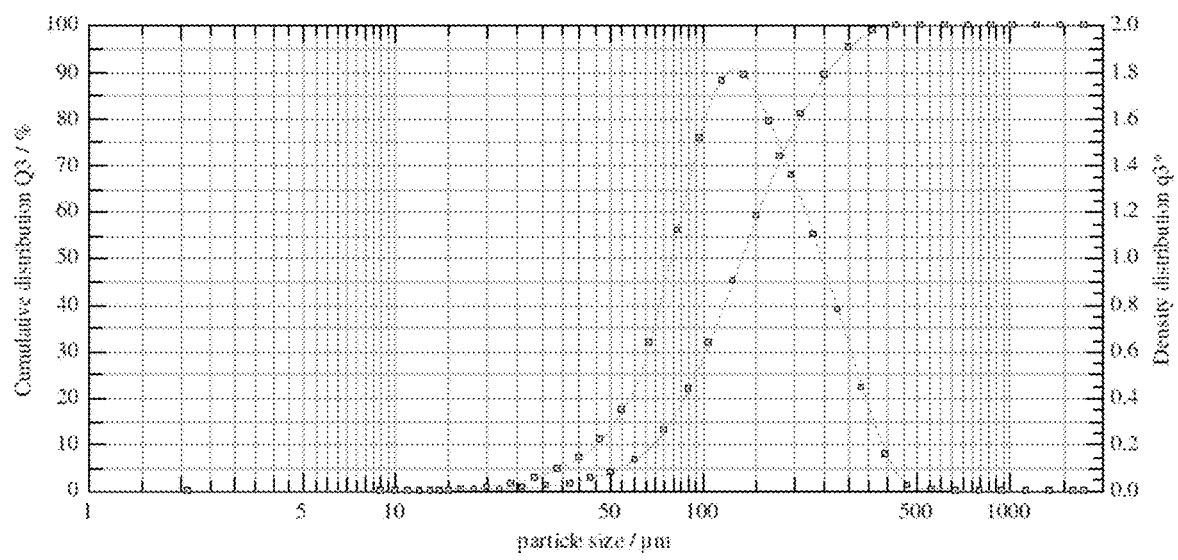
FIG. 13 is a graph of the cumulative and density distributions of droplet sizes produced by the TPU 8001 nozzle tip at 50 psi.

Data Underlying FIG. 13:
Height: 9.5 Nozzle: TPU—8001; Pressure: 50 psi; Copt=5.92%
HELOS (H2476) & SPRAYER, R6: 0.5/9.0 . . . 1750 μm
Volume Median Diameter: $D_{V0.5}$ 133.84 μm
Arithmetic Mean Diameter: D10 55.63 μm
Number Median Diameter: $D_{N0.5}$ 43.55 μm; $D_{V0.1}$ 68.39 μm; $D_{V0.9}$ 258.10 μm; $D_{V0.99}$ 379.56 μm
Surface Mean Diameter: D20 67.69 μm
Volume Mean Diameter: D30 80.69 μm
Surface-Dia. Mean Diameter: D21 82.35 μm
Evaporative Mean Diameter: D31 97.17 μm
Relative Span Factor: RSF 1.42
Sauter Mean Diameter: D32 114.66 μm

TABLE 13

Cumulative Distribution data underlying the graph in FIG. 13

| Diameter (μm) | Volume (%) |
|---|---|
| 9.00 | 0.00 |
| 11.00 | 0.00 |
| 13.00 | 0.00 |
| 15.00 | 0.00 |
| 18.00 | 0.05 |
| 22.00 | 0.18 |
| 26.00 | 0.41 |

TABLE 13-continued

Cumulative Distribution data underlying the graph in FIG. 13

| Diameter (μm) | Volume (%) |
|---|---|
| 31.00 | 0.82 |
| 37.00 | 1.52 |
| 43.00 | 2.45 |
| 50.00 | 3.86 |
| 60.00 | 6.60 |
| 75.00 | 12.72 |
| 90.00 | 21.55 |
| 105.00 | 31.69 |
| 125.00 | 44.99 |
| 150.00 | 59.07 |
| 180.00 | 71.62 |
| 210.00 | 80.68 |
| 250.00 | 88.99 |
| 300.00 | 95.15 |
| 360.00 | 98.63 |
| 430.00 | 99.86 |
| 510.00 | 100.00 |
| 610.00 | 100.00 |
| 730.00 | 100.00 |
| 870.00 | 100.00 |
| 1030.00 | 100.00 |
| 1230.00 | 100.00 |
| 1470.00 | 100.00 |
| 1750.00 | 100.00 |

Figure 14:
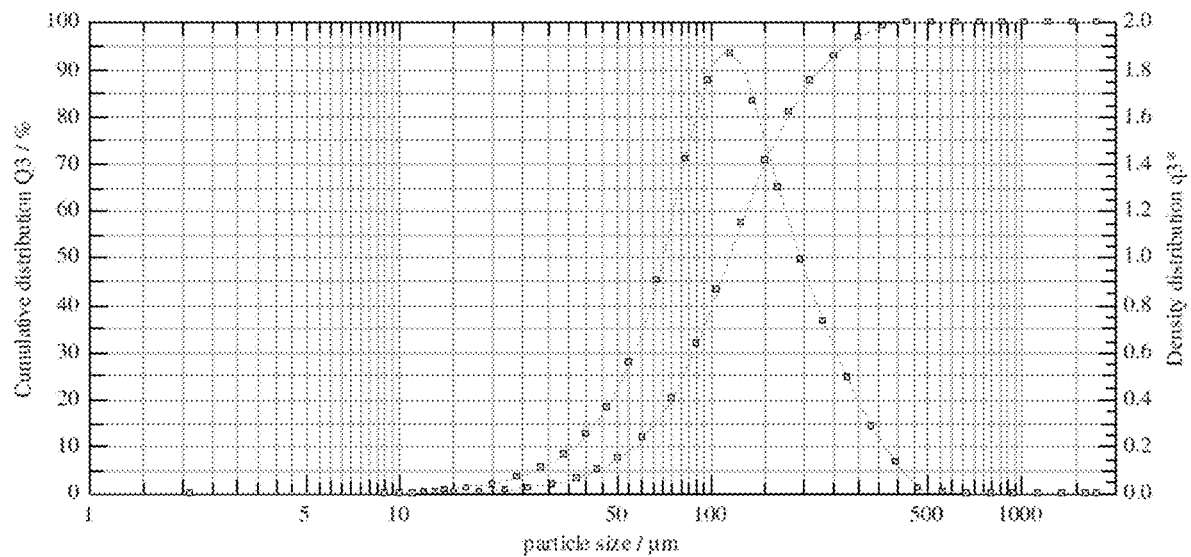
FIG. 14 is a graph of the cumulative and density distributions of droplet sizes produced by the TPU 8001 nozzle tip at 80 psi.

Data Underlying FIG. 14:
Height: 9.5 Nozzle: TPU—8001; Pressure: 80 psi; Copt=8.14%
HELOS (H2476) & SPRAYER, R6: 0.5/9.0 . . . 1750 μm
Volume Median Diameter: $D_{V0.5}$ 114.70 μm
Arithmetic Mean Diameter: D10 42.15 μm
Number Median Diameter: $D_{N0.5}$ 31.12 μm; $D_{V0.1}$ 56.61 μm; $D_{V0.9}$ 229.45 μm; $D_{V0.99}$ 368.18 μm
Surface Mean Diameter: D20 52.72 μm
Volume Mean Diameter: D30 64.47 μm
Surface-Dia. Mean Diameter: D21 65.96 μm
Evaporative Mean Diameter: D31 79.74 μm
Relative Span Factor: RSF 1.51
Sauter Mean Diameter: D32 96.40 μm

TABLE 14

Cumulative Distribution data underlying the graph in FIG. 14

| Diameter (μm) | Volume (%) |
|---|---|
| 9.00 | 0.00 |
| 11.00 | 0.00 |
| 13.00 | 0.02 |
| 15.00 | 0.10 |
| 18.00 | 0.27 |
| 22.00 | 0.61 |
| 26.00 | 1.09 |
| 31.00 | 1.88 |
| 37.00 | 3.14 |
| 43.00 | 4.78 |
| 50.00 | 7.17 |
| 60.00 | 11.51 |
| 75.00 | 20.22 |
| 90.00 | 31.43 |
| 105.00 | 43.14 |
| 125.00 | 57.23 |
| 150.00 | 70.42 |
| 180.00 | 80.71 |
| 210.00 | 87.30 |
| 250.00 | 92.83 |
| 300.00 | 96.67 |
| 360.00 | 98.88 |
| 430.00 | 99.87 |
| 510.00 | 100.00 |
| 610.00 | 100.00 |
| 730.00 | 100.00 |
| 870.00 | 100.00 |
| 1030.00 | 100.00 |
| 1230.00 | 100.00 |
| 1470.00 | 100.00 |
| 1750.00 | 100.00 |

Figure 15:
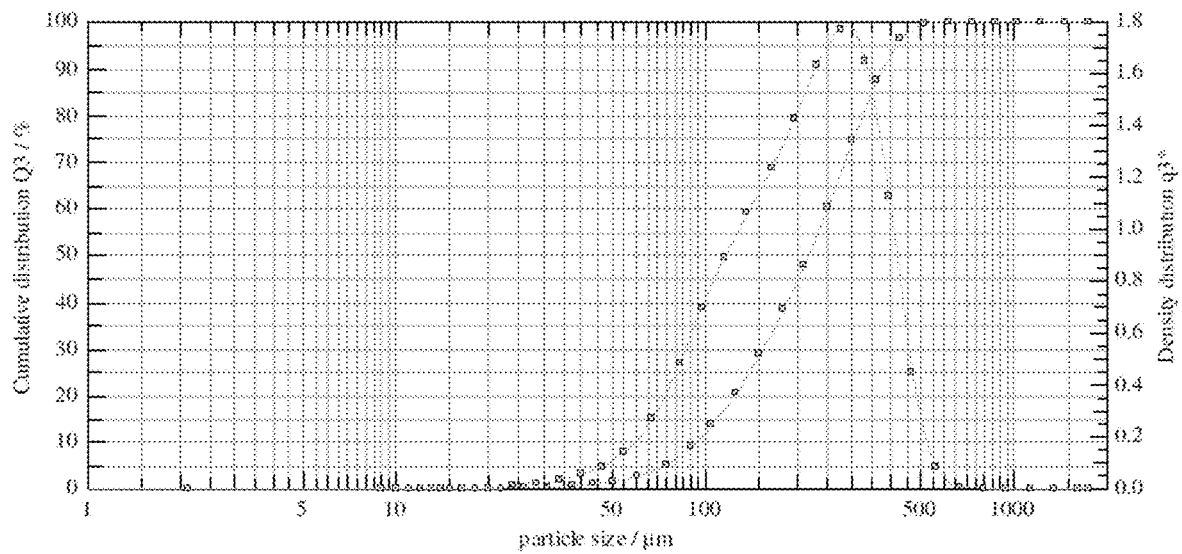
FIG. 15 is a graph of the cumulative and density distributions of droplet sizes produced by the TPU 8002 nozzle tip at 30 psi.

Data Underlying FIG. 15:
Height: 9.5 Nozzle: TPU—8002; Pressure: 30 psi; Copt=4.89%
HELOS (H2476) & SPRAYER, R6: 0.5/9.0 . . . 1750 μm
Volume Median Diameter: $D_{V0.5}$ 216.59 μm Arithmetic Mean Diameter: D10 74.64 μm
Number Median Diameter: $D_{N0.5}$ 58.61 μm Surface Mean Diameter: D20 92.51 μm
$D_{V0.1}$ 93.65 μm Volume Mean Diameter: D30 113.18 μm
$D_{V0.9}$ 381.13 μm Surface-Dia. Mean Diameter: D21 114.67 μm
$D_{V0.99}$ 501.69 μm Evaporative Mean Diameter: D31 139.36 μm
Relative Span Factor: RSF 1.33 Sauter Mean Diameter: D32 169.37 μm

TABLE 15

Cumulative Distribution data underlying the graph in FIG. 15

| Diameter (μm) | Volume (%) |
|---|---|
| 9.00 | 0.00 |
| 11.00 | 0.00 |
| 13.00 | 0.00 |
| 15.00 | 0.00 |
| 18.00 | 0.00 |
| 22.00 | 0.00 |
| 26.00 | 0.07 |
| 31.00 | 0.22 |
| 37.00 | 0.47 |
| 43.00 | 0.82 |
| 50.00 | 1.36 |
| 60.00 | 2.47 |
| 75.00 | 5.05 |
| 90.00 | 8.86 |
| 105.00 | 13.54 |
| 125.00 | 20.26 |
| 150.00 | 28.66 |
| 180.00 | 38.42 |
| 210.00 | 47.97 |
| 250.00 | 60.31 |
| 300.00 | 74.33 |
| 360.00 | 87.39 |
| 430.00 | 96.04 |
| 510.00 | 99.34 |
| 610.00 | 99.99 |
| 730.00 | 100.00 |
| 870.00 | 100.00 |
| 1030.00 | 100.00 |
| 1230.00 | 100.00 |
| 1470.00 | 100.00 |
| 1750.00 | 100.00 |

Figure 16:
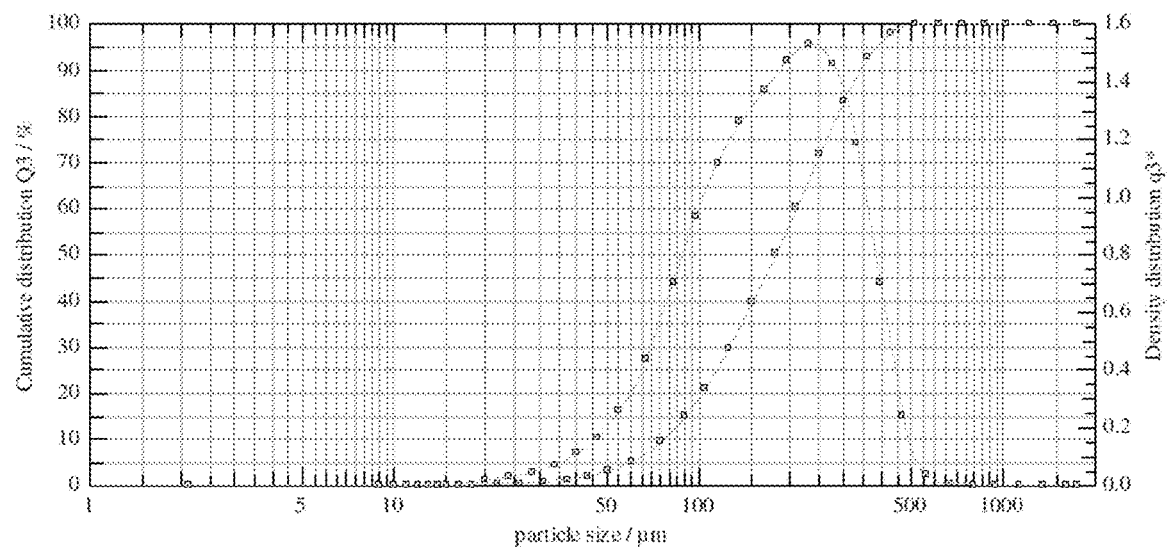
FIG. 16 is a graph of the cumulative and density distributions of droplet sizes produced by the TPU 8002 nozzle tip at 50 psi.

Data Underlying FIG. 16:
Height: 9.5 Nozzle: TPU—8002; Pressure: 50 psi; Copt=6.80%
HELOS (H2476) & SPRAYER, R6: 0.5/9.0 . . . 1750 μm
Volume Median Diameter: $D_{V0.5}$ 179.43 μm Arithmetic Mean Diameter: D10 58.11 μm
Number Median Diameter: $D_{N0.5}$ 43.75 μm; $D_{V0.1}$ 77.27 μm; $D_{V0.9}$ 343.79 μm; $D_{V0.99}$ 476.67 μm
Surface Mean Diameter: D20 72.93 μm
Volume Mean Diameter: D30 90.73 μm
Surface-Dia. Mean Diameter: D21 91.52 μm
Evaporative Mean Diameter: D31 113.36 μm
Relative Span Factor: RSF 1.49
Sauter Mean Diameter: D32 140.43 μm

TABLE 16

Cumulative Distribution data underlying the graph in FIG. 16

| Diameter (μm) | Volume (%) |
|---|---|
| 9.00 | 0.00 |
| 11.00 | 0.00 |
| 13.00 | 0.00 |
| 15.00 | 0.00 |
| 18.00 | 0.00 |
| 22.00 | 0.11 |
| 26.00 | 0.30 |
| 31.00 | 0.62 |
| 37.00 | 1.15 |
| 43.00 | 1.86 |
| 50.00 | 2.92 |
| 60.00 | 4.94 |
| 75.00 | 9.17 |
| 90.00 | 14.73 |
| 105.00 | 20.97 |
| 125.00 | 29.40 |
| 150.00 | 39.37 |
| 180.00 | 50.21 |
| 210.00 | 60.03 |
| 250.00 | 71.58 |
| 300.00 | 83.14 |
| 360.00 | 92.54 |
| 430.00 | 97.97 |
| 510.00 | 99.73 |
| 610.00 | 100.00 |
| 730.00 | 100.00 |
| 870.00 | 100.00 |
| 1030.00 | 100.00 |
| 1230.00 | 100.00 |
| 1470.00 | 100.00 |
| 1750.00 | 100.00 |

Figure 17:
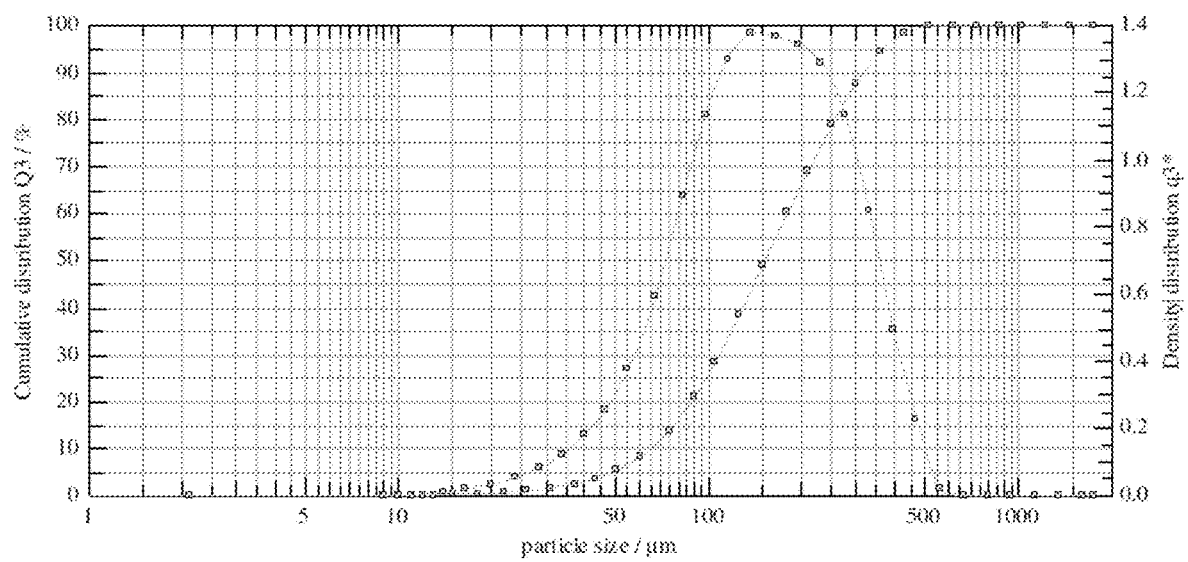
FIG. 17 is a graph of the cumulative and density distributions of droplet sizes produced by the TPU 8002 nozzle tip at 80 psi.

Data Underlying FIG. 17:
Height: 9.5 Nozzle: TPU—8002; Pressure: 80 psi; Copt=7.83%
HELOS (H2476) & SPRAYER, R6: 0.5/9.0 . . . 1750 μm; Volume Median Diameter: $D_{V0.5}$ 152.27 μm; Arithmetic Mean Diameter: D10 43.09 μm; Number Median Diameter: $D_{N0.5}$ 30.44 μm; $D_{V0.1}$ 64.93 μm; $D_{V0.9}$ 320.49 μm; $D_{V0.99}$ 467.33 μm; Surface Mean Diameter: D20 56.01 μm Volume Mean Diameter: D30 71.99 μm; Surface-Dia. Mean Diameter: D21 72.80 μm; Evaporative Mean Diameter: D31 93.06 μm; Relative Span Factor: RSF 1.68; Sauter Mean Diameter: D32 118.95 μm.

TABLE 17

Cumulative Distribution data underlying the graph in FIG. 17

| Diameter (μm) | Volume (%) |
|---|---|
| 9.00 | 0.00 |
| 11.00 | 0.00 |
| 13.00 | 0.00 |
| 15.00 | 0.05 |
| 18.00 | 0.20 |
| 22.00 | 0.47 |

TABLE 17-continued

Cumulative Distribution data underlying the graph in FIG. 17

| Diameter (μm) | Volume (%) |
|---|---|
| 26.00 | 0.84 |
| 31.00 | 1.44 |
| 37.00 | 2.36 |
| 43.00 | 3.53 |
| 50.00 | 5.19 |
| 60.00 | 8.15 |
| 75.00 | 13.87 |
| 90.00 | 20.92 |
| 105.00 | 28.49 |
| 125.00 | 38.32 |
| 150.00 | 49.19 |
| 180.00 | 59.99 |
| 210.00 | 68.97 |
| 250.00 | 78.72 |
| 300.00 | 87.69 |
| 360.00 | 94.41 |
| 430.00 | 98.20 |
| 510.00 | 99.87 |
| 610.00 | 100.00 |
| 730.00 | 100.00 |
| 870.00 | 100.00 |
| 1030.00 | 100.00 |
| 1230.00 | 100.00 |
| 1470.00 | 100.00 |
| 1750.00 | 100.00 |

DETAILED DESCRIPTION OF THE EMBODIMENTS

Figure 1A:
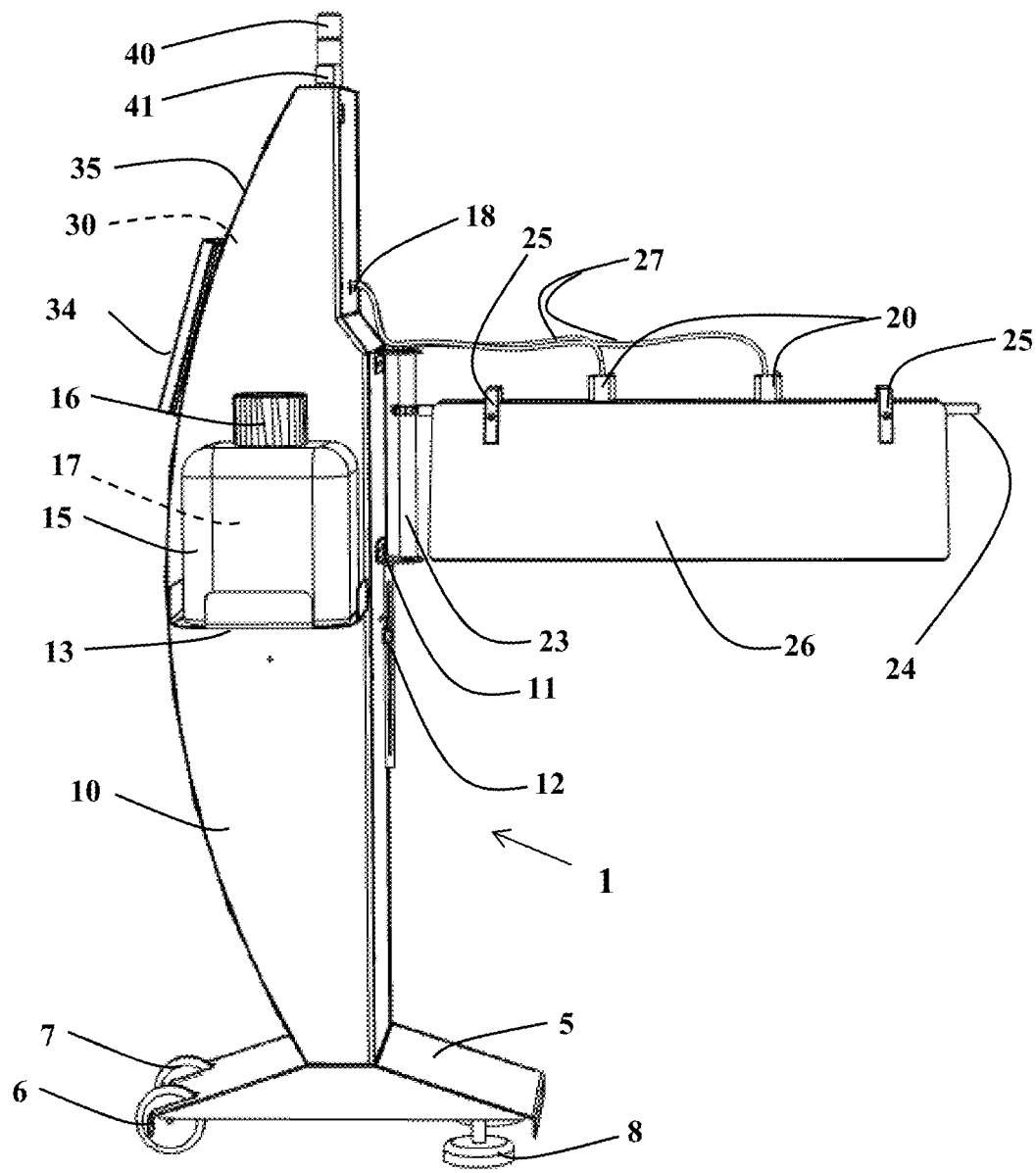
FIG. 1A shows a side-view of an inline spray applicator 1 equipped with rapidly actuatable automatic spray nozzles 20, according to the disclosure.
Figure 1B:
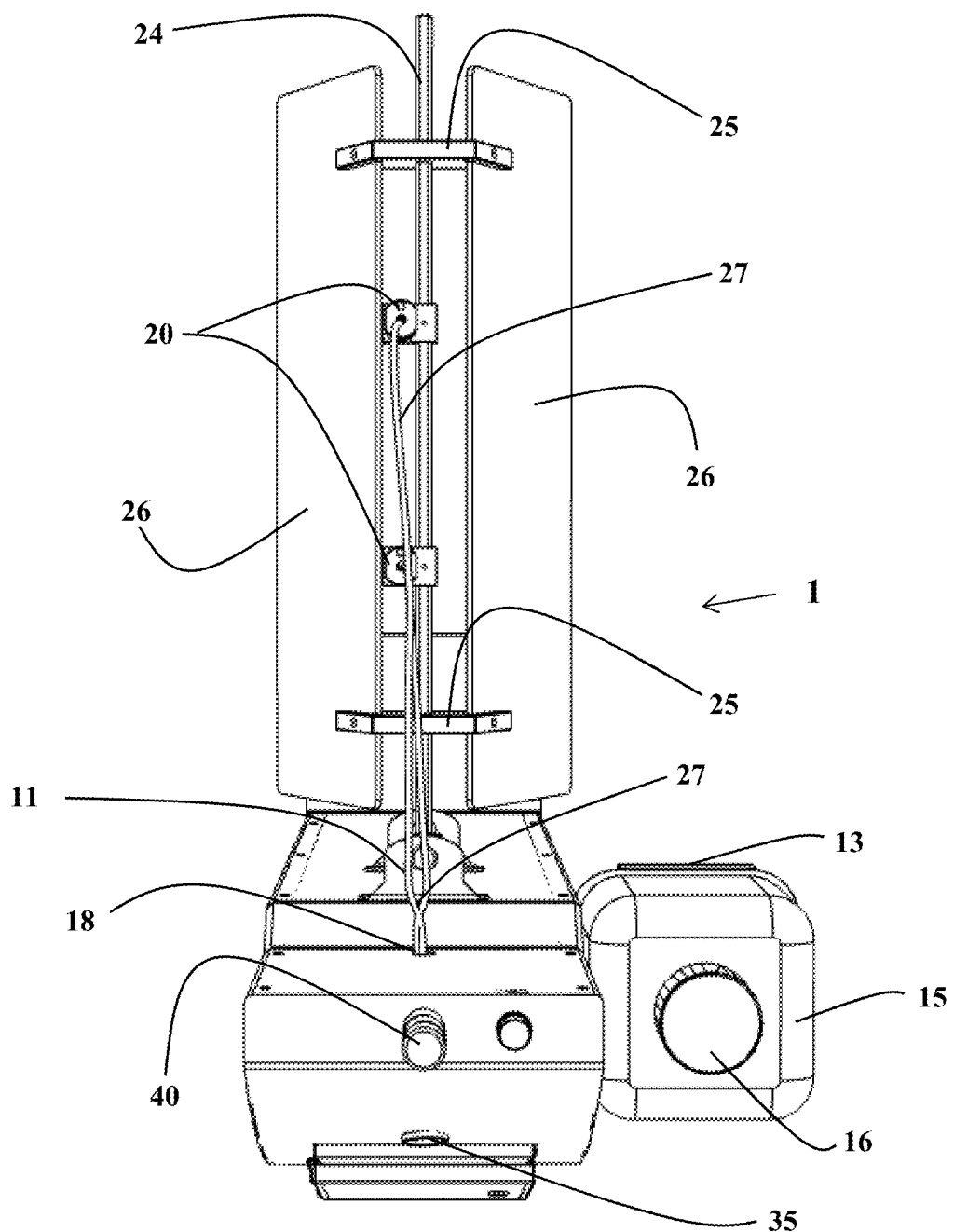
FIG. 1B shows a top-view of the inline spray applicator 1.
Figure 1C:
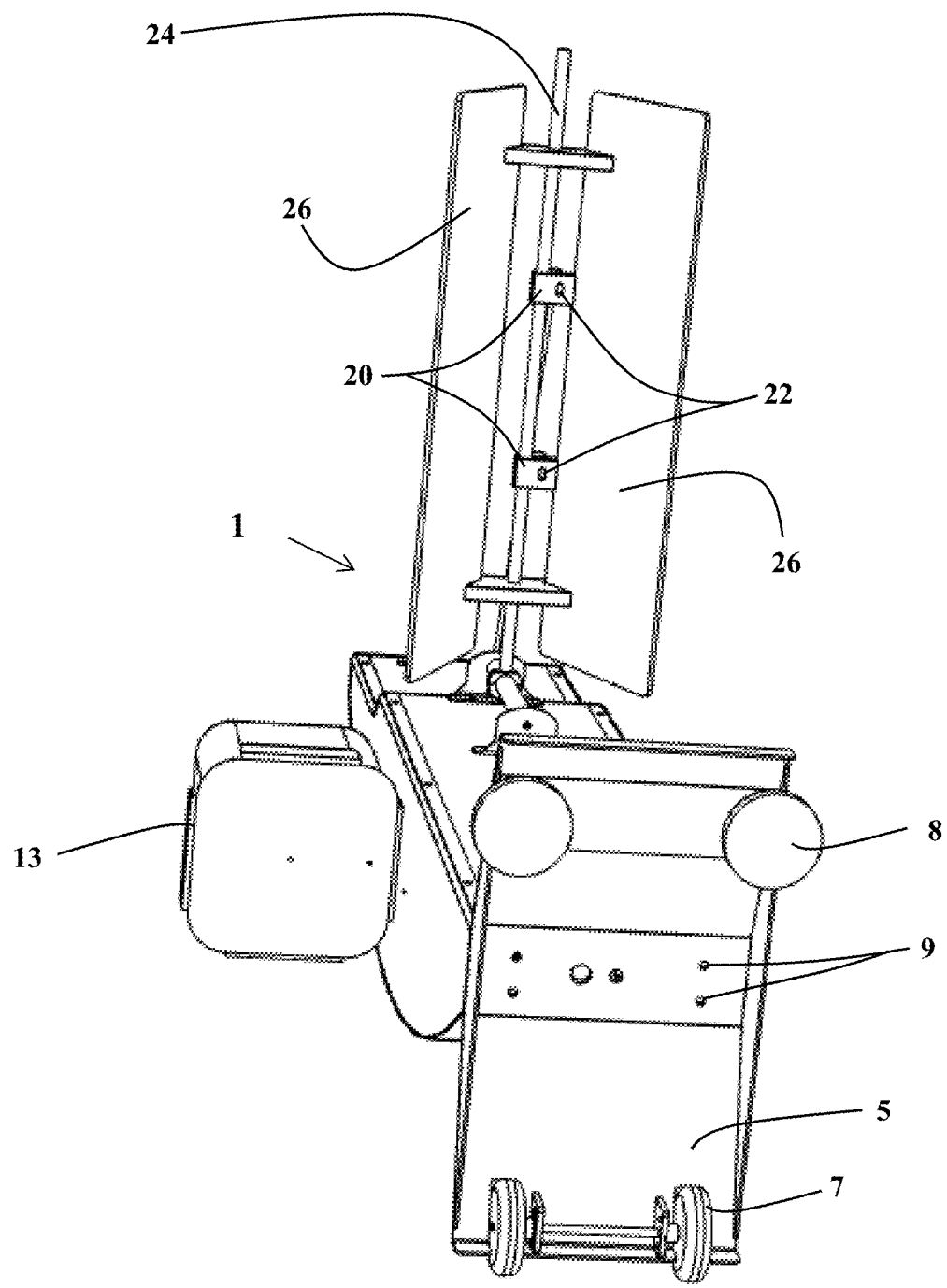
FIG. 1C shows a slightly offset bottom-view of the inline spray applicator 1.
Figure 1D:
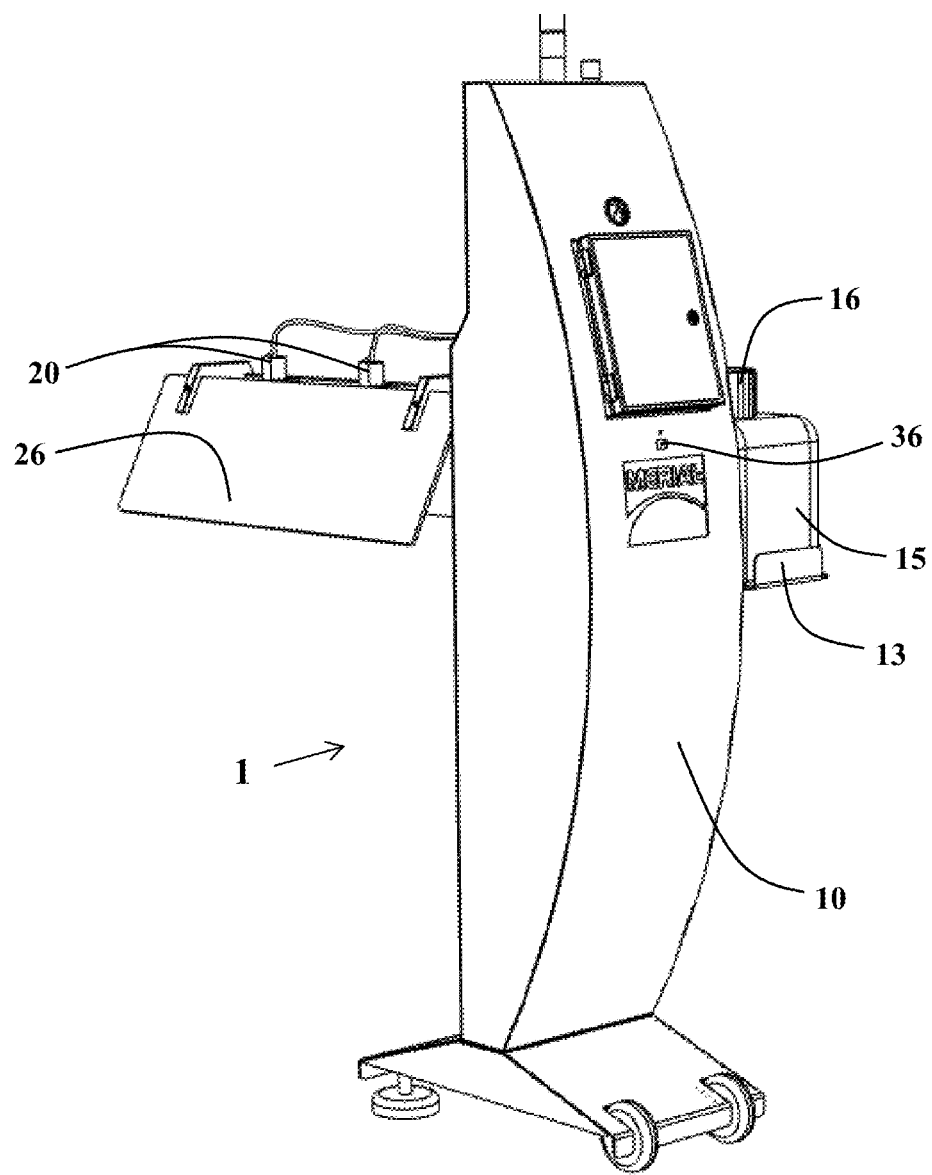
FIG. 1D shows a three-quarter rear-view of the inline spray applicator 1.
Figure 1E:
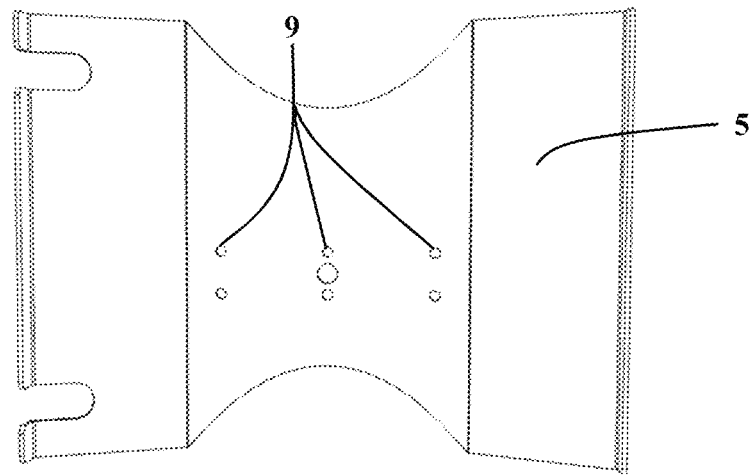
FIG. 1E shows an alternative embodiment of the base 5.
Figure 1F:
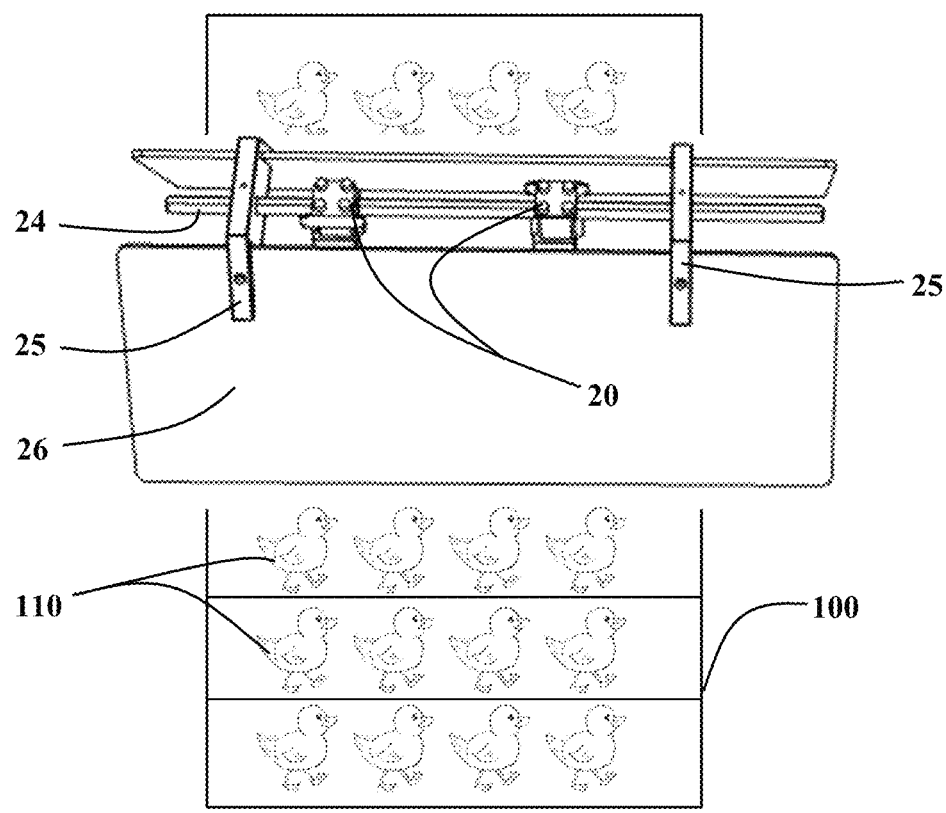
FIG. 1F is an overhead view of a portion of the spray applicator 1, shown with a basket 100 containing a plurality of chicks 110 to be sprayed.
Figure 1G:
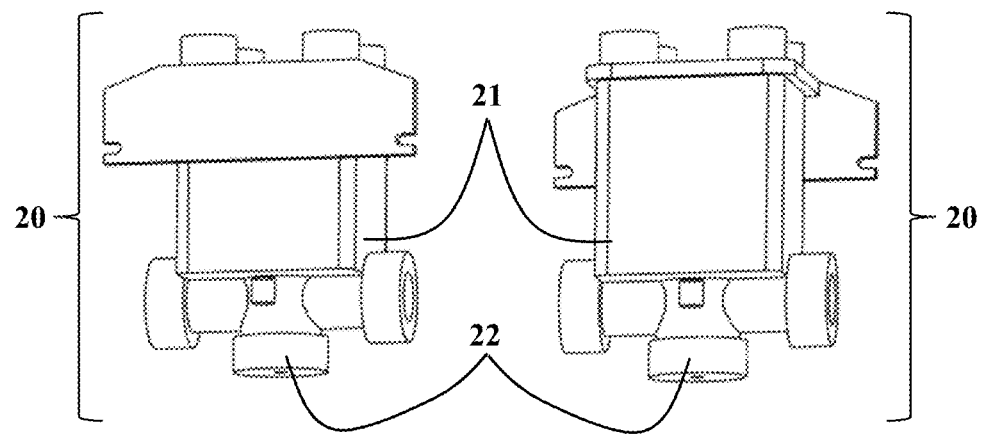
FIG. 1G shows a front and back view of an automatic spray nozzle 20.
Figure 1H:
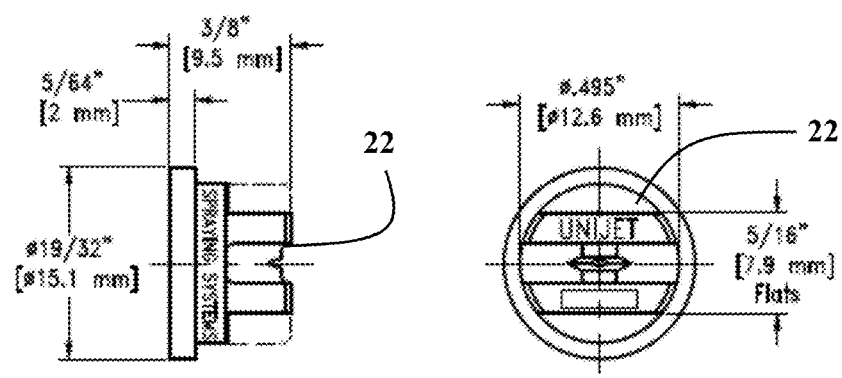
FIG. 1H shows a UniJet 8001E automatic spray nozzle tip 22, which produces a flat spray, has a capacity of 0.10 gallons per minute (GPM) at 40 PSI liquid pressure (with water), and has an 80 degree spray angle. These nozzle tips 22 may be made of brass, stainless steel or hardened stainless steel.
Figure 2:
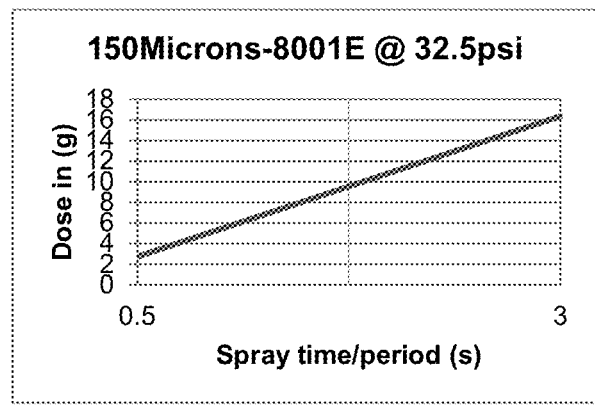
FIG. 2 is a graph showing dose volume vs. time. One nozzle test; 150 μM; nozzle tip 8001E @ 32.5 psi.
Figure 3:
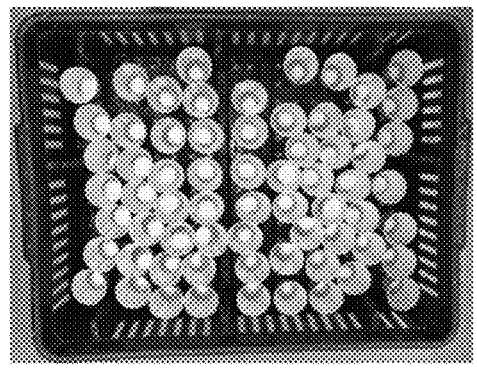
FIG. 3 shows the results of the spray distribution test. Seven (7) mL of water was delivered via 30 shots, from nozzle tip 8001E @ 32.5 psi, to a typical poultry basket/crate, containing 66 collection cups.
Figure 4:
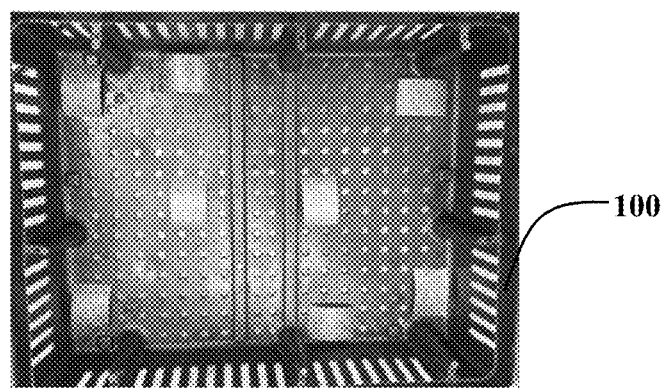
FIG. 4 shows the droplet size delivered by the 8001E nozzle tip @ 32.5 psi to water-sensitive paper placed throughout a typical poultry basket/crate.
Figure 5:
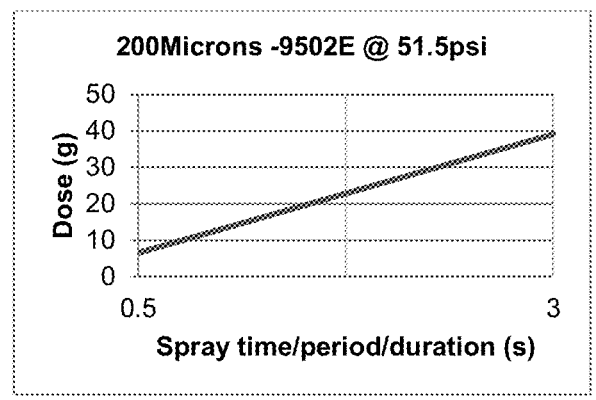
FIG. 5 is a graph showing dose volume vs. time. One nozzle test; 200 μM; Nozzle tip 9502E @ 51.5 psi.
Figure 6:
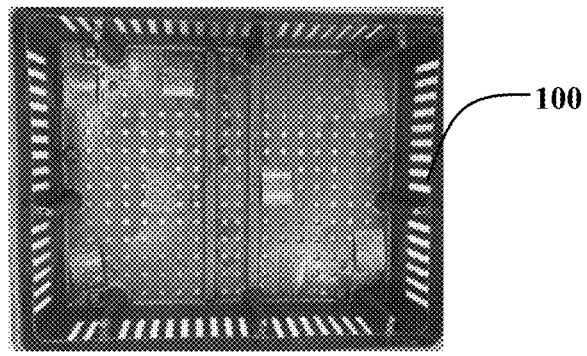
FIG. 6 shows the droplet size delivered by the 9502E nozzle tip @ 51.5 psi to water-sensitive paper placed throughout a typical poultry basket. Spray Distribution at 15.6 mL.
Figure 7:
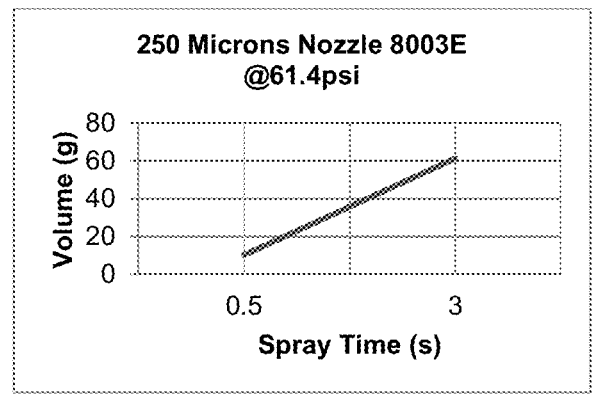
FIG. 7 is a graph showing dose volume vs. time. One nozzle test; 250 μM; 8003E nozzle tip @ 51.5 psi.
Figure 8:
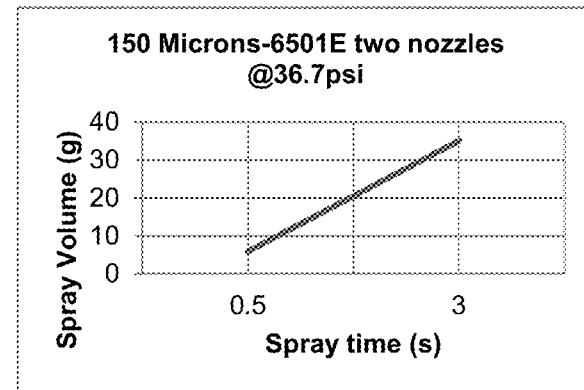
FIG. 8 is a graph showing dose volume vs. time. Two nozzle test; 150 μM; two 6501E nozzle tips @ 36.7 psi.
Figure 9:
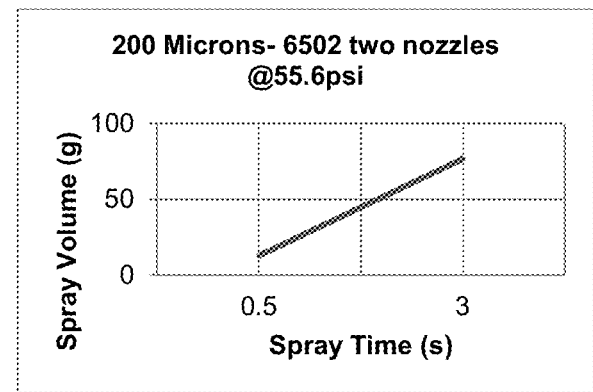
FIG. 9 is a graph showing dose volume vs. time. Two nozzle test; 200 μM; two 6502E nozzle tips @ 55.6 psi.
Figure 10:
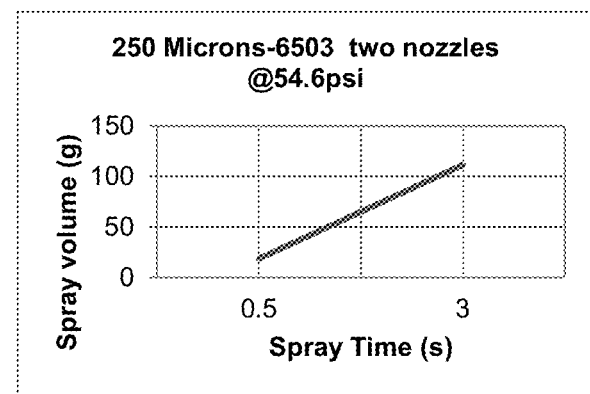
FIG. 10 is a graph showing dose volume vs. time. Two nozzle test; 250 μM; two 6503E nozzle tips @ 54.6 psi.

FIG. 1A shows a side-view of a spray applicator 1 equipped with rapidly actuatable spray nozzles 20, according to the disclosure. All numbers refer to the same parts, unless otherwise expressly stated. The applicator comprises a base 5, comprising a rolling means 6 (e.g. a wheel or caster or the like) for facilitating the movement of the applicator from one location (e.g. a storage location) to another location (e.g. a use location). Use locations include places in hatcheries where crates/baskets containing young avian animals are being transported along a conveyor system. The base 5 may further comprise a rolling means locking means 7 (e.g. a friction brake) for preventing the rolling means 6 from rolling. In addition to the locking means 7, the base 5 may also comprise a standing means 8 (e.g. feet, including deployable and adjustable feet) for maintaining the applicator in a fixed position when movement of the applicator is not desired (e.g. when the applicator is in its storage or use location).

As shown, the applicator comprises a housing 10, which is attached to and supported by the base 5. In an embodiment, the housing 10 attaches to the base by the fixing of nuts and bolts through base openings 9. The base openings 9 align with corresponding openings on the bottom portion of the housing 10. The housing 10 comprises a tank holder 13 for holding a tank 15. The tank or has a lid 16 comprising a safety blow off valve, and is in fluid communication with a programmable spray module 30 (for controlling the amount and timing of liquid sprayed by the nozzles), which is itself in electrical, pneumatic or hydraulic connection with one or a plurality of actuatable automatic spray nozzles 20. The nozzles 20 are fluidly connected to the tank via conduits 27 that pass through the housing 10 via orifice 18. Electrical connectivity, including wires, may be employed to electrically connect the automatic spray nozzles 20 to the module 30, such that the module 30 may be programmed to control the opening and closing of the automatic spray nozzles 20. The tank 15 may further comprise a level liquid float 17. The flow of fluid may be functionally connected to a sensor 12, which is capable of relaying/communicating a fluid flow status (e.g. lack of flow, low pressure, high pressure, and the like) to a user via the spray module 30 or via a light indicator 40.

Further attached to the housing 10, via a rod attachment means 11, is a vertical nozzle hood assembly adjustment rod 23. Attached to the vertical rod 23 is a horizontal nozzle hood adjustment rod 24, which attaches to hood panels 26 via hood panel attachment means 25 (e.g. a hood mounting plate, having slots for receiving the panels). At the top of the applicator housing 10 is a vaccine or other fluid alarm status indicator light tower 40 and a pressure regulator 41. Below the pressure regulator 44 is a pressure gauge indicator 35, and below that is an access hatch 34, which provides secure access to the programmable spray module 30. The spray module 30 is operable and programmable via a touch screen 31, which is attached thereto. Situated on the housing 10 and below the hatch 34 is an "on" indicator 36 and an "on/off" switching means 37.

A user may input commands into the spray module 30 to regulate the amount and timing of liquid that is sprayed through the automatic spray nozzle 20 and onto a plurality of young avian animals 110. As shown in FIG. 1F, the avian animals may be young chicks 110 contained within a poultry hatchery-style basket 100, or other suitable means for transporting chicks in a hatchery, including along a conveyor system, including a conveyor belt.

In an advantageous embodiment, the spray applicator 1 is positioned above a hatchery conveyor belt, which is transporting young avian animals 110 to be vaccinated. The nozzle 20 height and positioning (e.g. up/down, nearer/farther from one another, near/farther away from the spray applicator housing 10) are adjusted to optimize the delivery of liquids, including vaccines and probiotic formulations, to the avian animals 110. Many routine configurations of the automatic spray nozzles will become apparent to the skilled person now that the instant disclosure has been made.

In a particular embodiment, either the 8001E and 6501E nozzle tip may be used to achieve the desired droplet size of about 150 microns. In one embodiment, the 8001E nozzle tip is used for low volume hatcheries and slower conveyor speeds. As indicated in the Figures, the maximum dose for the 8001E nozzle tip at 32.5 psi to achieve 150 microns is about 16 ml.

In another embodiment, for hatcheries that use higher delivery volumes (e.g. about 21 mL) and faster conveyor speeds, two 6501E nozzle tips (i.e. three automatic spray nozzles equipped with 6501E nozzle tips) at 36.7 psi may be used, to achieve the higher dose at the given conveyor speed, since the 6501E nozzle tips are limited to about 0.096 GPM.

In yet another embodiment, three 6501E nozzle tips (i.e. three automatic spray nozzles equipped with 6501E nozzle tips) may be used to achieve a higher dose volume or to accommodate a faster conveyor speed.

Other embodiments will become apparent to the skilled person in view of the foregoing disclosure.

What is claimed:

1. An automated spray applicator configured for administrating a liquid biologic to young avian animals, comprising:

a housing;

a first and a second actuatable automatic spray nozzle, each nozzle comprising a stationary nozzle tip that produces droplets of the liquid biologic, such that greater than 90% of the droplets have diameters sized from about 125 to about 300 microns based on a fluid pressure from about 30 psi to about 80 psi, each stationary nozzle tip produces a 65 degree spray angle at 40 psi, and the first nozzle is positioned to spray towards the second nozzle at about 45 degrees from vertical; and a programmable spray control module programmed to actuate the first and second actuatable automatic spray nozzles between open and closed positions, wherein the programmable spray control module is in electrical, pneumatic or hydraulic connection with the first and second actuatable automatic spray nozzles;

wherein the first and second actuatable automatic spray nozzles are in fluid communication with a fluid tank containing the liquid biologic.

2. The spray applicator of claim 1, wherein each nozzle tip is a 6501E nozzle tip and wherein the nozzle tip produces droplets of 150 microns during use.

3. The spray applicator of claim 1, further comprising a base, wherein the base comprises a standing means, for maintaining the applicator in a fixed position when movement of the applicator is not desired.

4. The spray applicator of claim 1, wherein a tank holder is mounted to the housing.

5. The spray applicator of claim 4, wherein the tank comprises a fluid level float and a lid.

6. The spray applicator of claim 1, wherein the flow of fluid is functionally connected to a sensor, wherein the sensor relays/communicates a fluid flow status to a user via the spray module or via a light indicator during use.

7. The spray applicator of claim 1, wherein a vertical nozzle hood assembly adjustment rod is connected to the housing via a rod attachment means.

8. The spray applicator of claim 7, wherein attached to the vertical rod is a horizontal nozzle hood adjustment rod, which attaches to vaccine hood panels via vaccine hood panel attachment means.

9. The spray applicator of claim 8, comprising a vaccine or other fluid alarm status indicator light tower and a pressure regulator, situated at a top-most portion of the housing.

10. The spray applicator of claim 1, wherein the spray module is operable and programmable via a touch screen.

11. A method for administering vaccine or non-vaccine fluid to day old chicks, or other young avian animals, comprising administering vaccine or other non-vaccine fluid to said chicks or other avian animals using the spray applicator of claim 1, thereby administering the vaccine or non-vaccine fluid.

12. A method of treating chicks, or other young avian animals, with a probiotic formulation comprising the steps of dispersing the probiotic formulation using the spray applicator of claim 1; and allowing the chicks to consume the dispensed probiotic formulation, thereby treating the chicks or other young avian animals.

13. The method of claim 12, wherein the probiotic formulation is a liquid or liquid-like gel.

14. The spray applicator of claim 1 further comprising a source of pressurized air for supplying pressure to the fluid prior to its entry into the spray nozzle.

15. The spray applicator of claim 1, wherein the applicator is mounted to a base, which base comprises a rolling means for facilitating the movement of the applicator from one location to another location.

16. The spray applicator of claim 15, wherein the rolling means comprises a locking means to reversibly prevent the rolling means from rolling during use.

\* \* \* \* \*